United States Patent [19]

Nishikido et al.

[11] Patent Number: 4,465,668

[45] Date of Patent: Aug. 14, 1984

[54] METHOD FOR IMPROVING INTESTINAL ABSORPTION OF CEPHALOSPORIN DERIVATIVES

[75] Inventors: Joji Nishikido; Eiji Kodama, both of Fuji; Mitsuru Shibukawa, Yokohama, all of Japan

[73] Assignee: Asahi Kasei Kogyo Kabushiki Kaisha, Osaka, Japan

[21] Appl. No.: 351,613

[22] Filed: Feb. 24, 1982

[30] Foreign Application Priority Data

Feb. 27, 1981 [JP] Japan .................................. 56-26743
Aug. 19, 1981 [JP] Japan ................................ 56-128688

[51] Int. Cl.³ ............................................. A61K 37/02
[52] U.S. Cl. ................................................... 424/177
[58] Field of Search .............................. 424/177, 271; 260/112.5 R

[56] References Cited

U.S. PATENT DOCUMENTS

| | | | |
|---|---|---|---|
| 3,925,370 | 12/1975 | Wei et al. ............................ | 424/271 |
| 3,929,781 | 12/1975 | Teller et al. .......................... | 424/271 |
| 4,087,424 | 5/1978 | Saikawa et al. ...................... | 424/271 |
| 4,112,090 | 9/1978 | Saikawa et al. ...................... | 424/271 |
| 4,162,314 | 7/1979 | Gottschlick et al. ................ | 424/271 |
| 4,276,288 | 6/1981 | Etschenberg et al. ........ | 260/112.5 R |

OTHER PUBLICATIONS

Wheeler, J. of Med. Chem., vol. 22, No. 6, 657–661 (1979).

*Primary Examiner*—Delbert R. Phillips
*Assistant Examiner*—F. Moezie
*Attorney, Agent, or Firm*—Finnegan, Henderson, Farabow, Garrett & Dunner

[57] ABSTRACT

A method for improving the intestinal absorption of a cephalosporin derivative by bonding an oligopeptide having the general formula (I):

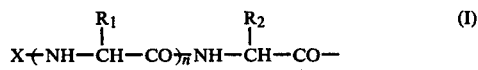

wherein
X is a hydrogen atom, $C_{1-15}$ alkyl group, $R_3CO$— group wherein $R_3$ is a hydrogen atom or straight or branched chain $C_{1-15}$ alkyl group or a protective group easily removable by acid hydrolysis, hydrogenolysis or enzyme existing in a living body;
$R_1$ and $R_2$ each independently is a side chain of an amino acid constituting the oligopeptide; and
n is integer of 1 to 3, to any side chain at the 3-, 4- or 7-position of a 7-aminocephalosporanic acid derivative having antibacterial activity.

10 Claims, No Drawings

METHOD FOR IMPROVING INTESTINAL ABSORPTION OF CEPHALOSPORIN DERIVATIVES

This invention relates to a method for improving the intestinal absorption of cephalosporin derivatives. More specifically, this invention relates to a method for improving the intestinal absorption of 7-aminocephalosporanic acid derivatives having antibacterial activity by bonding an oligopeptide with the cephalosporanic acid derivatives.

Most semi-synthetic cephalosporin compounds actually used as a drug for remedy or prevention of infectious disease have little oral activity. In contrast with penicillin, the method for improving the intestinal absorption of cephalosporin has not been found. Therefore, in the medical treatment by administering this drug to patients, a trained medical expert has been required. Accordingly, development of cephalosporin antibiotic which can be orally administered and has strong antibacterial activities has been greatly desired, and many studies have been done for a long period of time. Most reports of the studies relate to making lipo-soluble cephalosporin derivatives by esterifying the 4-position carboxylic acid group of cephalosporin compounds. As the lipo-soluble cephalosporin derivatives, the acetoxymethyl ester derivative, the pivaloyloxymethyl ester derivative and the methoxymethyl ester derivative are reported. However, these cephalosporin derivatives have not been put to practical use because of their low oral activity.

According to J. of Med. Chem. 22, 657 (1979), it is reported that the amino acid acyloxymethyl ester of 7-[D-(—)-mandelamido]-3-[[(1-methyl-1H-tetrazol-5-yl)thio]methyl]-3-cephem-4-carboxylic acid having the formula:

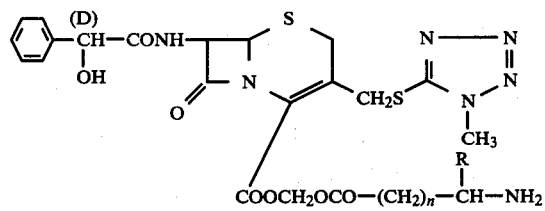

wherein
R is

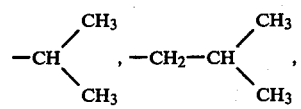

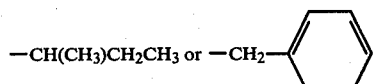

when n=0; and R is —COOH when n=1; shows no improved efficiency when this ester is administered orally.

The present invention provides the method for modifying a cephalosporin derivative to improve the intestinal absorption of a cephalosporin derivative comprising bonding a group having the general formula (I):

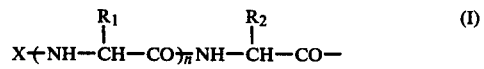

wherein
X is a hydrogen atom, $C_{1-15}$ alkyl group, $R_3CO$— group wherein $R_3$ is a hydrogen atom or straight or branched chain $C_{1-15}$ alkyl group or a protective group easily removable by acid hydrolysis, hydrogenolysis or enzyme existing in a living body;

$R_1$ and $R_2$ each independently is a side chain of an amino acid constituting the group having the general formula (I); and n is integer of 1 to 3, to any side chain at the 3-, 4- or 7-position of a 7-aminocephalosporanic acid derivative having antibacterial activity.

Any 7-aminocephalosporanic acid derivatives having antibacterial activity can be employed in this invention. Preferred 7-aminocephalosporanic acid derivatives can be represented by the general formula (II);

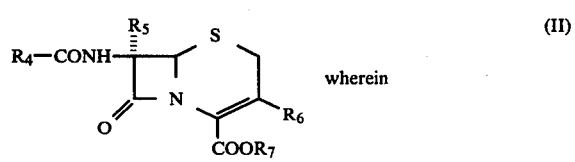

wherein $R_4$ is

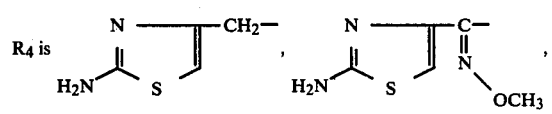

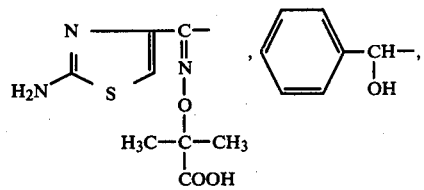

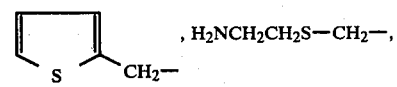

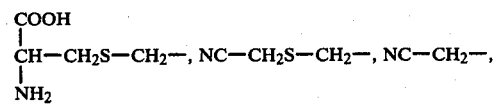

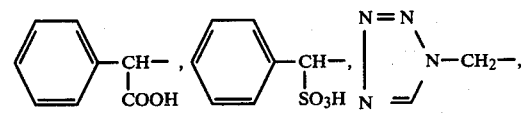

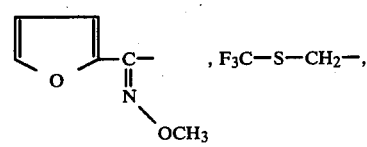

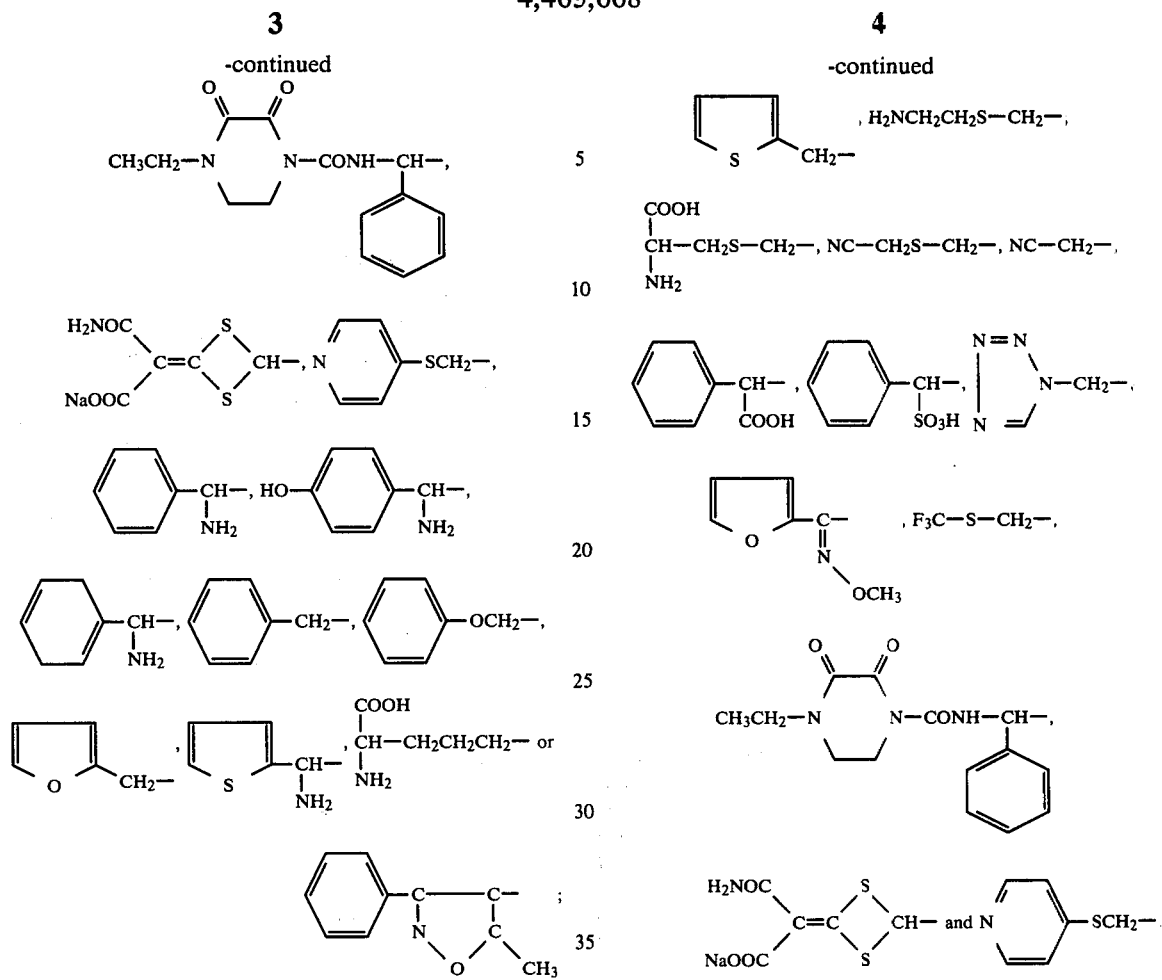

$R_5$ is a hydrogen atom or a methoxy group;
$R_6$ is —CH$_3$, —Cl, —OCH$_3$, —H, —CH$_2$OCOCH$_3$, —CH$_2$OCONH$_2$ or —CH$_2$SHet. wherein Het. is a 5- to 6-membered heterocyclic ring containing therein 1 to 4 nitrogen, oxygen or sulfur atoms; and $R_7$ is a hydrogen atom, an alkali metal, an alkaline earth metal, an organic amino group or a protective group for the carboxyl group.

Preferred $R_4$ of the formula (II) includes

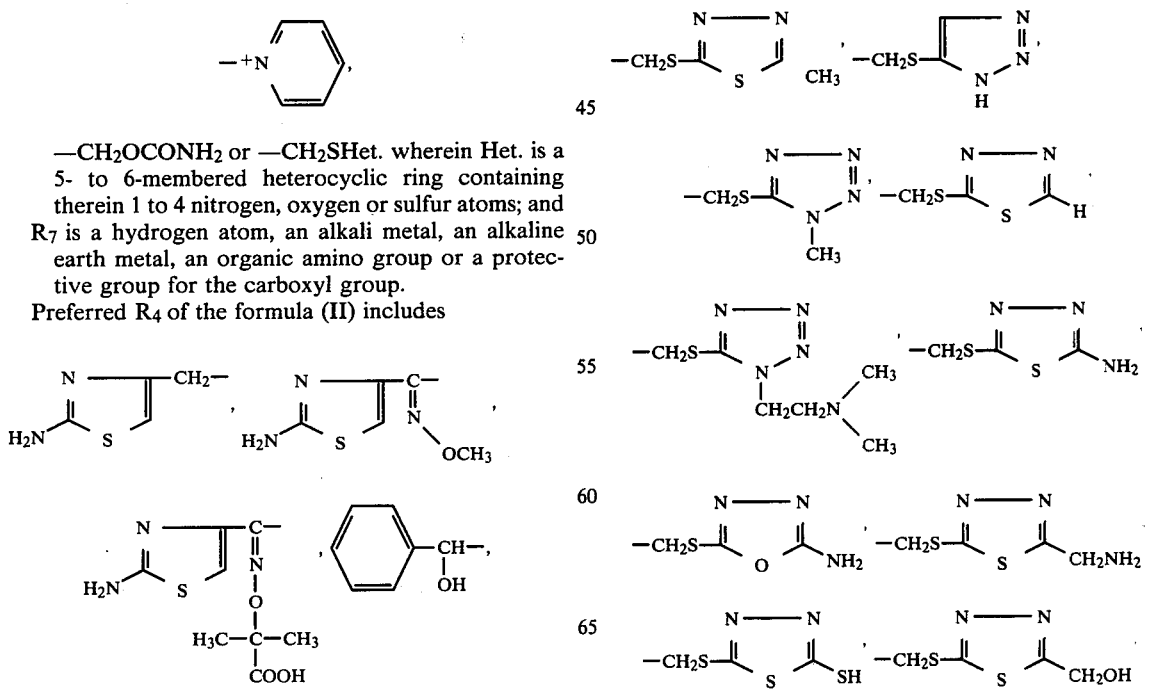

Exemplary —CH$_2$SHet. in $R_6$ of the formula (II) which can be employed includes -continued

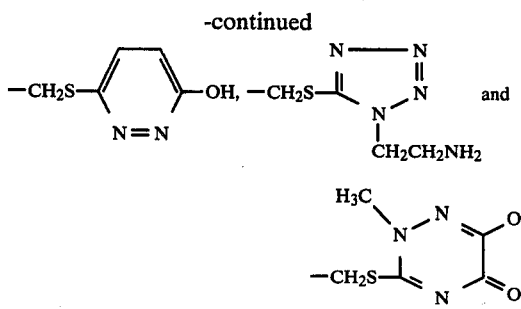

The protective groups for the carboxyl group in $R_7$ of the formula (II) which can be employed include —CH$_2$OCH$_3$, —CH$_2$OCOCH$_3$, —CH$_2$OCO—C(CH$_3$)$_3$, —CH(CH$_3$)OCOOC$_2$H$_5$ and

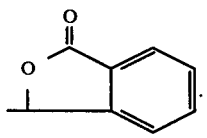

The oligopeptide having the general formula (I) is bonded to any side chain at the 3-, 4- or 7-position of the 7-aminocephalosporanic acid derivative. Preferred groups which can be reacted with the oligopeptides and contained in the side chains at the 3-, 4- or 7-position of the 7-aminocephalosporanic acid derivatives include an amino group, a hydroxyl group, a phenyl group, a mercapto group and a halogen atom.

Preferred X in the formula (I) includes a hydrogen atom and a formyl group.

Exemplary $R_1$ and $R_2$ include a hydrogen atom, an unsubstituted straight or branched chain $C_{1-10}$ alkyl group, a straight or branched chain $C_{1-10}$ alkyl group which is substituted by at least one group selected from the group consisting of a hydroxyl group, a mercapto group, a methylthio group, an amino group, a phenyl group, a phenoxy group, a hydroxyphenyl group, a carboxyl group, an indolyl group, an azide group, a halogen atom, a cyano group, a $C_{1-4}$ alkoxy group, a $C_{1-4}$ alkylthio group, a nitro group, a trifluoromethyl group, a guanidino group, a $C_{3-6}$ cyclic hydrocarbon group and a 5- to 6-membered heterocyclic ring containing therein 1 to 5 nitrogen, oxygen or sulfur atoms; and a hydrocarbon whose terminal carbon atom is bonded with the nitrogen atom of the amino acid to form a nitrogen-containing heterocyclic ring.

Preferred $R_1$ and $R_2$ include a hydrogen atom, an unsubstituted straight or branched chain $C_{1-4}$ alkyl group, a straight or branched chain $C_{1-4}$ alkyl group which is substituted by a hydroxyl group, a mercapto group, a methylthio group, an amino group, a phenyl group, a hydroxyphenyl group, a carboxyl group, an indolyl group, $C_{1-4}$ alkylthio group, a guanidino group or a 5- to 6-membered heterocyclic ring containing therein 1 to 5 nitrogen atoms, and a $C_{3-5}$ hydrocarbon whose terminal carbon atoms is bonded with the nitrogen atoms of the amino acid to form a nitrogen-containing heterocyclic ring.

Exemplary amino acids having $R_1$ or $R_2$ as the side chain include alanine, isoleucine, leucine, methionine, valine, phenylalanine, tyrosine, phenylglycine, tryptophan, lysine, ornithine, histidine, arginine, serine, threonine, glutamic acid, aspartic acid, cysteine, α-aminoadipic acid, proline, α-amino-n-butyric acid and glycine. Of these amino acids, L-isomers of the amino acids are more preferable if the amino acids have both D- and L-isomers.

Preferred n in the formula (I) is one.

The oligopeptide of formula (I) is bonded to any side chain at the 3-, 4- or 7-position of the 7-aminocephalosporanic acid derivative at the carbon terminal of the oligopeptide. The 7-aminocephalosporanic acid derivatives which can be obtained by bonding the oligopeptide of the formula (I) to any side chain at the 3-, 4- or 7-position of the 7-aminocephalosporanic acid derivative of the formula (II) at the carbon terminal of the oligopeptide are novel compounds and have improved intestinal absorption. This novel compounds are useful as an antibacterial drug which can be orally administered.

The method for bonding the oligopeptide to the 7-aminocephalosporanic acid derivative comprises protecting the nitrogen terminal of the oligopeptide and reacting the protected oligopeptide with 7-aminocephalosporanic acid derivative using a condensation agent in the presence of a solvent. Prior to the reaction, the protected oligopeptide can be changed to the reactive derivative by reacting the protected oligopeptide with a mixed acid anhydride having a reactive group such as iso-butyloxycarbonyl group and pivaloyl group or a reactive ester such as p-nitrophenol and N-hydroxysuccinimide.

Exemplary condensation agents which can be employed in the reaction between the oligopeptide and the 7-aminocephalosporanic acid derivative include N,N'-dicyclohexylcarbodiimide, 1-ethyl-3-(3-dimethylaminopropyl)carbodiimide hydrochloric acid salt and N,N'-carbonyldiimidazole.

Exemplary solvents which can be employed in the reaction between the oligopeptide and the 7-aminocephalosporanic acid derivative include water, acetone, ethyl ether, ethyl acetate, chloroform, dichloromethane, acetonitril, dioxane, dimethyl sulfoxide, tetrahydrofuran, N,N'-dimethylformamide and any mixture thereof.

The amount of the oligopetide which can be employed is preferably about one mol per mol of the 7-aminocephalosporanic acid derivative, however, excess amount of the oligopeptide or the 7-aminocephalosporanic acid derivative can be employed, if necessary.

The reaction temperature and the reaction period of time which can be employed in the reaction between the oligopeptide and the 7-aminocephalosporanic acid derivative depend on the reaction method. In general, the reaction can be carried out at a temperature of from about −50° C. to about 80° C. and preferably from about −20° C. to about 50° C. The reaction period of time which can be usually employed in the reaction is from about 5 minutes to about 100 hours.

The novel compounds obtained by bonding the oligopeptide (I) to the 7-aminocephalosporanic acid derivative can be orally administered singly or with a pharmaceutically acceptable carrier or dilution agent. Exemplary carriers and dilution agents include lactose, saccharose, starch, cellulose, calcium sulfate and gelatin. The novel compounds can be administered in the form of a tablet, a capsule, a suspension or a solution. According to this invention, the cephalosporin derivatives might be directly absorbed in intestinal membranes through absorption channels existing therein for oligopeptide. This absorption mechanism is very different from that of the conventional lipo-soluble cephalosporin derivatives. In the conventional method, the lipo-soluble cephalosporin derivatives are absorbed from the lipid double layers of intestinal membranes by their chemical attraction. The method of this invention is useful because this method can be applied to other pharmaceuticals having poor oral activity.

The absorption test of the compounds were measured by the following methods.

ABSORPTION TEST

Male Wistar rats weighing 180–250 g were fed with only water overnight. The next day the rats were orally administered with 50 mg/kg of a test compound which was suspended in a 0.7% CMC aqueous solution. The concentration of the compound in the tested animals (one group consisting of 5 animals) was measured 0.5, 1, 2 and 4 hours after the administration by Bioassay method by using Bacillus subtilis ATCC 6633 strain as an indicator bacteria. In the measurement, an ordinary culture medium was employed, and the preparation of the standard solution and other method were carried out in according to Japanese Antibiotical Pharmaceutical Standards. Further, the concentration of the compound in blood was also measured by high performance liquid chromatography. The blood concentration shown in the examples was an average value of each animal group.

The following examples illustrate the present invention in more detail, but they are given for illustrative purposes only and are not to be construed as limiting the invention. The abbreviations used in the examples show the following amino acids.

| α-AAA | α-Aminoadipic Acid | α-ABA | α-Amino-n-butyric Acid |
|---|---|---|---|
| Ala | Alanine | Arg | Arginine |
| Asp | Aspartic Acid | Cys | Cysteine |
| Glu | Glutamic Acid | Gly | Glycine |
| His | Histidine | Ile | Isoleucine |
| Leu | Leucine | Lys | Lysine |
| Met | Methionine | Orn | Ornithine |
| Phe | Phenylalanine | PheGly | Phenylglycine |
| Pro | Proline | Ser | Serine |
| Thr | Threonine | Trp | Tryptophan |
| Tyr | Tyrosine | Val | Valine |

EXAMPLE 1

7-D-(O-L-leucyl-L-phenylalanyl)-mandelamido-3-(1-methyl-1H-tetrazol-5-yl-thiomethyl)-3-cephem-4-carboxylic acid formic acid salt was prepared in accordance with the following equations:

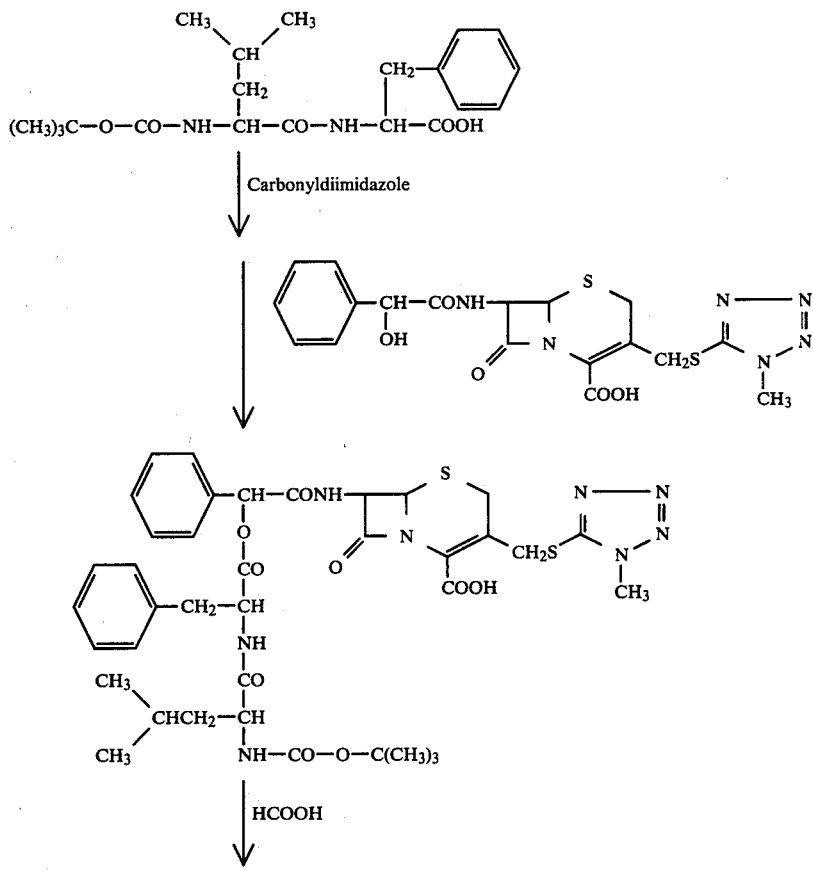

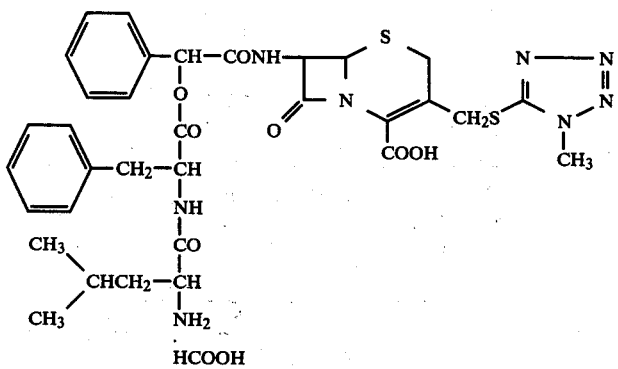

In 10 ml of anhydrous tetrahydrofuran were dissolved 0.76 g of tert-butyloxycarbonyl-L-leucyl-L-phenylalanine and 0.32 g of N,N'-carbonyldiimidazole, and the reaction was carried out at 20° C. for 30 minutes. To the reaction solution was added 0.92 g of 7-D-mandelamido-3-(1-methyl-1H-tetrazol-5-yl-thiomethyl)-3-cephem-4-carboxylic acid [Compound (I)] dissolved in 5 ml of anhydrous tetrahydrofuran, and the reaction was carried out at 20° C. out for 72 hours. After completion of the reaction, tetrahydrofuran was removed under reduced pressure. To the residue thus obtained was added 50 ml of ethyl acetate to form precipitates.

The precipitates were separated by filtration and added into a mixture of 30 ml of water and 100 ml of ethyl acetate cooled with ice and then the pH of the mixed solution was adjusted to 2 with hydrochloric acid. The ethyl acetate layer was separated and washed with water, and then dried with sodium sulfate. Further, the ethyl acetate layer was concentrated under reduced pressure. The compound thus obtained was dissolved in 30 ml of formic acid and the reaction was carried out at 20° C. for 2 hours. After completion of the reaction, formic acid was removed under reduced pressure and then 30 ml of ethyl acetate was added to the residue to give 0.59 g of light orange crystals.

These crystals were identified as 7-D-(O-L-leucyl-L-phenylalanyl)-mandelamido-3-(1-methyl-1H-tetrazol-5-yl-thiomethyl)-3-cephem-4-carboxylic acid formic acid salt by the following NMR spectrum of the crystals.

NMR Spectrum (in DMSO substituted by heavy hydrogen):

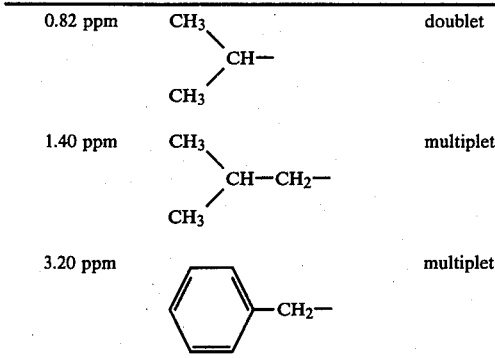

| 3.92 ppm | N—N (ring with CH₃) | singlet |
| 4.34 ppm | —CH₂S— (ring with CH₃) | multiplet |
| 4.92 ppm | 6 - H | doublet |
| 5.60 ppm | 7 - H | multiplet |
| 6.10 ppm | phenyl-CH—CO—O— | singlet |
| 7.15 ppm | phenyl-CH₂— | multiplet |

The absorption test results of 7-D-(O-L-leucyl-L-phenylalanyl)mandelamido-3-(1-methyl-1H-tetrazol-5-yl-thiomethyl)-3-cephem-4-carboxylic acid formic acid salt are as follows:

|  | 0.5 hr. | 1 hr. | 2 hrs. | 4 hrs. |
| --- | --- | --- | --- | --- |
| Blood concentration of Compound (I) (μg/ml) | 4.51 | 3.70 | 1.93 | 0.83 |

EXAMPLES 2-7

The same procedures as described in Example 1 were repeated except that other oligopeptides were employed instead of the tert-butyloxycarbonyl-L-leucyl-L-phenylalanine. As a result, the cephalosporin derivatives having the oligopeptides as set forth in Table 1 were obtained. The absorption test results of the compounds thus obtained are shown in Table 1.

TABLE 1

| Example No. | Oligopeptide | | | | Blood Concentration of Compound (I) (μg/ml) | | | |
|---|---|---|---|---|---|---|---|---|
| | X | Amino Acid Unit Containing $R_1$ | Amino Acid Unit Containing $R_2$ | n | 0.5 hr. | 1 hr. | 2 hrs. | 4 hrs. |
| 2 | H | Phe | Leu | 1 | 2.03 | 1.41 | 0.87 | 0.23 |
| 3 | HCO | Phe | Phe | 1 | 1.03 | 1.88 | 1.76 | 1.01 |
| 4 | H | Met(D) | Met | 1 | 0.49 | 0.59 | 0.31 | 0.09 |
| 5 | $CH_3CO$ | Leu | Phe | 1 | 0.41 | 0.98 | 1.01 | 0.03 |
| 6 | H | Leu | Lys | 1 | 4.98 | 3.96 | 2.30 | 1.04 |
| 7 | HCO | Leu | Met | 1 | 0.78 | 1.43 | 0.86 | 0.43 |
| Comparative | (none) | | | | 0.29 | 0.16 | 0.10 | 0.09 |

Note:
(1) (D) shows the D-isomer of the amino acid. Amino acids without the indication show the L-isomers.
(2) In Comparative Example Compound (I) was employed in the absorption test.

COMPARATIVE EXAMPLE 1

The same procedures as described in Example 1 were repeated except that formyl-L-phenylalanine was employed instead of the tert-butyloxycarbonyl-L-leucyl-L-phenylalanine. The absorption test results of the compound thus obtained (7-D-(O-L-phenylalanyl)-mandelamido-3-(1-methyl-1H-tetrazol-5-yl-thiomethyl)-3-cephem-4-carboxylic acid formic acid salt) are as follows:

| | 0.5 hr. | 1 hr. | 2 hrs. | 4 hrs. |
|---|---|---|---|---|
| Blood Concentration of Compound (I) (μg/ml) | 0.21 | 0.23 | 0.08 | 0.02 |

EXAMPLE 8

7-[2-(2-thienyl)-acetoamido]-3-[2-(L-propyl-L-lysylaminomethyl-1,3,4-thiadiazolyl)-thiomethyl]-3-cephem-4-carboxylic acid formic acid salt was prepared in accordance with the following equations:

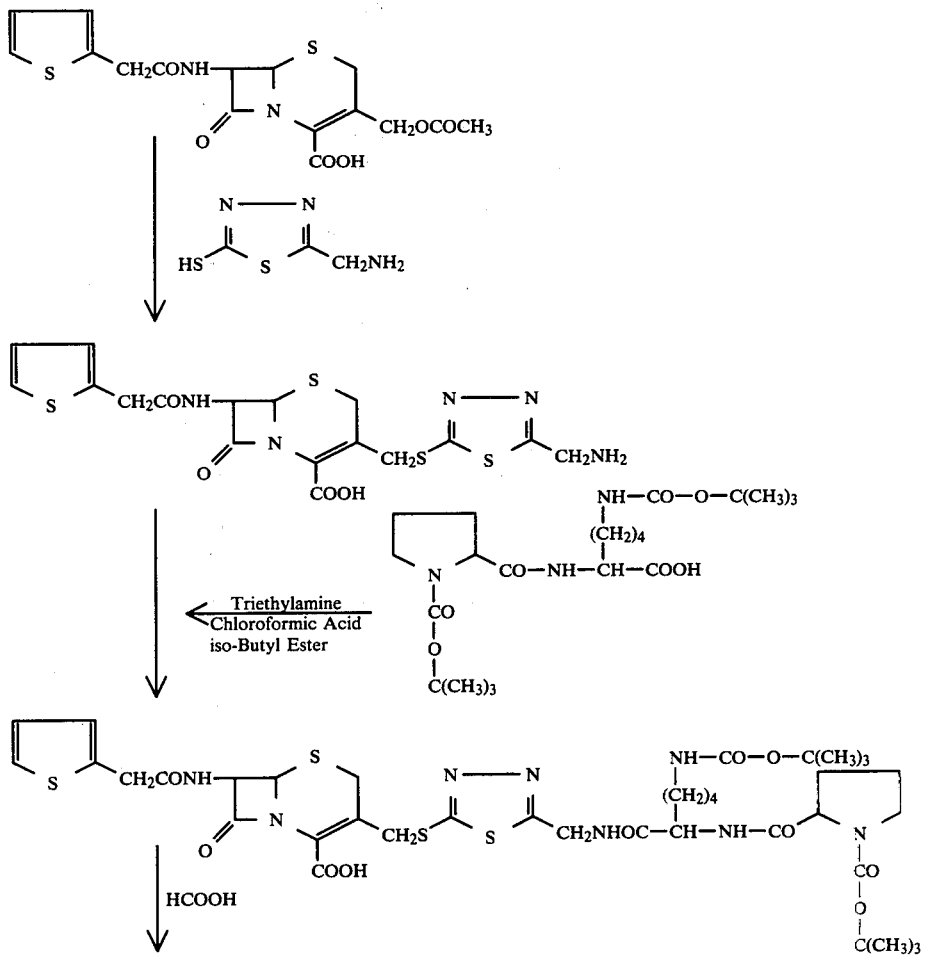

-continued

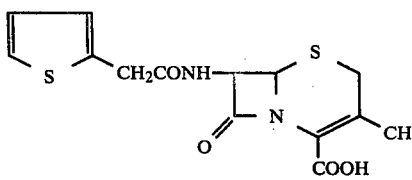 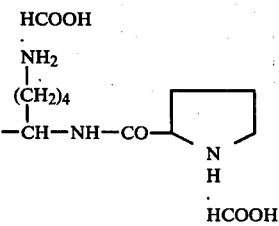

To 50 ml of water were added 1 g of 7-[2-(2-thienyl)-acetoamido]-3-acetoxymethyl-3-cephem-4-carboxylic acid and 1.3 g of 2-aminomethyl-5-mercapto-1,3,4-thiadiazole. The reaction was carried out at 60°–70° C. for 5 hours in a nitrogen gas atmosphere while the pH of the reaction mixture was adjusted to 6.0–6.4. The crystals of 7-[2-(2-thienyl)-acetamido]-3-[2-(5-aminomethyl-1,3,4-thiadiazolyl)-thiomethyl]-3-cephem-4-carboxylic acid [Compound (II)] were precipitated during the reaction and the crystals were separated by filtration.

In 30 ml of tetrahydrofuran were dissolved 1.1 g of α-tert-butyloxycarbonyl-L-prolyl-ε-tert-butyloxycarbonyl-L-lysine and 0.25 g of triethylamine and to the solution was added 0.34 g of chloroformic acid iso-butyl ester at −10° C. After stirring the solution for 30 minutes, 1.3 g of the 7-[2-(2-thienyl)-acetoamido]-3-[2-(5-aminomethyl-1,3,4-thiadiazolyl)-thiomethyl]-3-cephem-4-carboxylic acid as obtained above and 0.25 g of triethylamine were added to the solution, and the reaction was carried out at −10° C. for one hour. Then the reaction solution was concentrated under reduced pressure and to the residue thus obtained were added 20 ml of ethyl acetate and 20 ml of water. The pH of the mixture was adjusted to 2 with hydrochloric acid and the ethyl acetate layer was washed with water and then dried. The solvent was removed from the layer to obtain 7-[2-(2-thienyl)-acetoamido]-3-[2-α-tert-butyloxycarbonyl-L-prolyl-ε-tert-butyloxycarbonyl-L-lysylaminomethyl-1,3,4-thiadiazolyl)-thiomethyl]-3-cephem-4-carboxylic acid.

The compound thus obtained was dissolved in 20 ml of formic acid and the reaction was carried out at 20° C. for one hour. Then the formic acid was removed under reduced pressure and to the residue was added 15 ml of ethyl ether with stirring to give precipitates. The precipitates formed were separated by filtration. The amount of the precipitates was 1.2 g.

The precipitates was identified as 7-[2-(2-thienyl)-acetoamido]-3-[2-(L-prolyl-L-lysylaminomethyl-1,3,4-thiadiazolyl)-thiomethyl]-3-cephem-4-carboxylic acid formic acid salt by the following NMR spectrum of the precipitates.

NMR Spectrum (in DMSO):

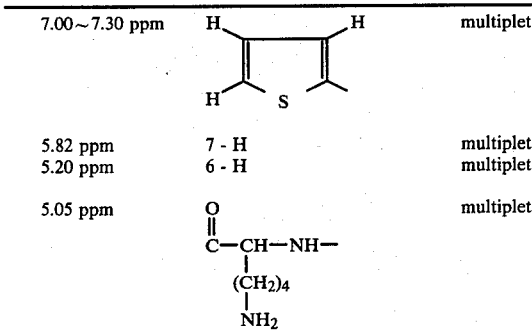

| | | |
|---|---|---|
| 7.00~7.30 ppm | (H H / H S) | multiplet |
| 5.82 ppm | 7-H | multiplet |
| 5.20 ppm | 6-H | multiplet |
| 5.05 ppm | O=C—CH—NH— / (CH₂)₄ / NH₂ | multiplet |

-continued

| | | |
|---|---|---|
| 4.84 ppm | OC(H)N (pyrrolidine) | multiplet |
| 4.70 ppm | —CH₂S— | multiplet |
| 4.02 ppm | N——N / S / CH₂—NH | singlet |
| 3.73 ppm | (thienyl)CH₂CO | multiplet |
| 3.62 ppm | —OC—N(H) (pyrrolidine) | multiplet |
| 3.30 ppm | (β-lactam S CH₂) | multiplet |
| 2.20 ppm | (pyrrolidine CH₂CH₂) | multiplet |
| 1.70 ppm | —CH— / (CH₂)₃ / CH₂ / NH₂ | multiplet |

The absorption test of 7-[2-(2-thienyl)-acetoamido]-3-[2-(L-prolyl-L-lysylaminomethyl-1,3,4-thiadiazolyl)-thiomethyl]-3-cephem-4-carboxylic acid formic acid salt was carried out by orally administering the salt which was dissolved in a buffer aqueous solution having the pH of 7. The results are as follows:

| | 0.5 hr. | 1 hr. | 2 hrs. | 4 hrs. |
|---|---|---|---|---|
| Blood Concentration of Compound (II) (μg/ml) | 2.14 | 1.77 | 1.04 | 0.07 |

EXAMPLES 9–14

The same procedures as described in Example 8 were repeated except that other oligopeptides were employed instead of the α-tert-butyloxycarbonyl-L-prolyl- ε-tert-butyloxycarbonyl-L-lysine. As a result, the cephalosporin derivatives having the oligopeptides as set forth in Table 2 were obtained. The absorption test of these compounds thus obtained was carried out in the same manner as described in Example 8. The results are shown in Table 2.

EXAMPLE 15

7-[2-(2-amino-4-thiazolyl)acetoamido-3-(5-methyl-1,3,4-thiadiazolyl)thiomethyl]-3-cephem-4-carboxylic acid L-leucyl-L-lysyloxymethyl ester hydrochloric acid salt was prepared in accordance with the following equations:

TABLE 2

| Example No. | Oligopeptide | | | | Blood Concentration of Compound (II) (μg/ml) | | | |
|---|---|---|---|---|---|---|---|---|
| | X | Amino Acid Unit Containing $R_1$ | Amino Acid Unit Containing $R_2$ | n | 0.5 hr. | 1 hr. | 2 hrs. | 4 hrs. |
| 9 | $CH_3(CH_2)_6CO$ | Leu | Phe | 1 | 0.07 | 0.11 | 0.04 | 0.01 |
| 10 | HCO | Trp | Phe | 1 | 1.21 | 0.90 | 0.32 | 0.05 |
| 11 | H | Leu | Glu | 1 | 2.00 | 1.67 | 0.22 | 0.03 |
| 12 | H | Met | Phe | 2 | 0.39 | 0.21 | 0.07 | <0.01 |
| 13 | H | Met | Phe | 1 | 1.63 | 0.64 | 0.09 | <0.01 |
| 14 | H | Leu | Thr | 1 | 1.24 | 0.79 | 0.24 | 0.06 |
| Comparative | | (none) | | | <0.01 | <0.01 | <0.01 | <0.01 |

Note:
(1) All the amino acids were the L-isomers.
(2) In Comparative Example Compound (II) was employed in the absorption test.

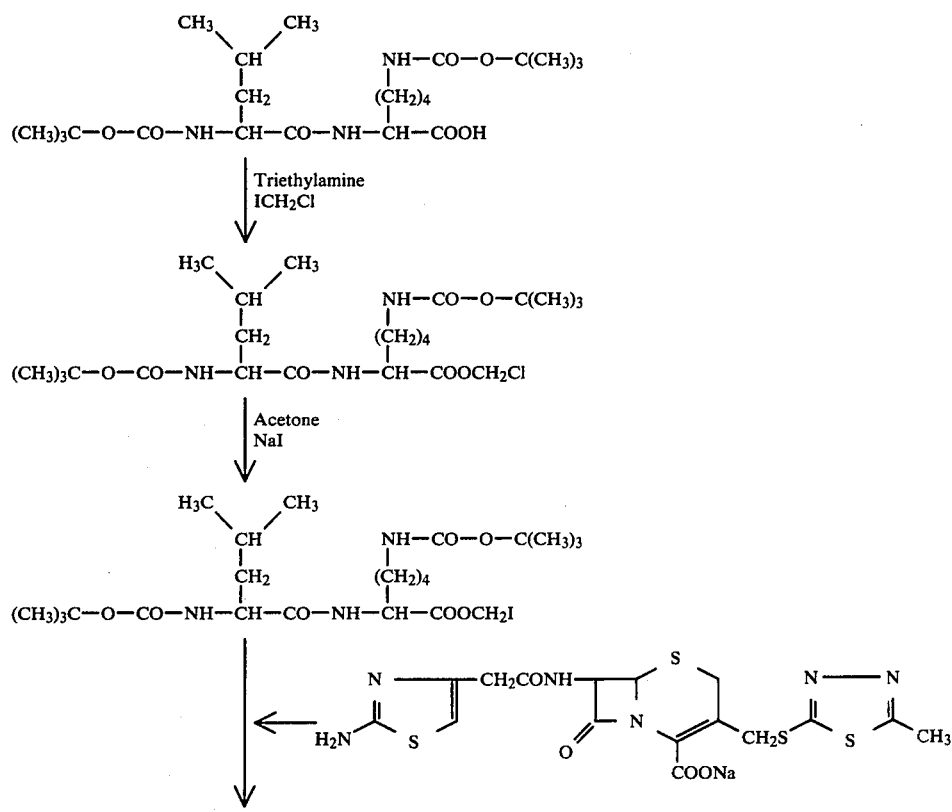

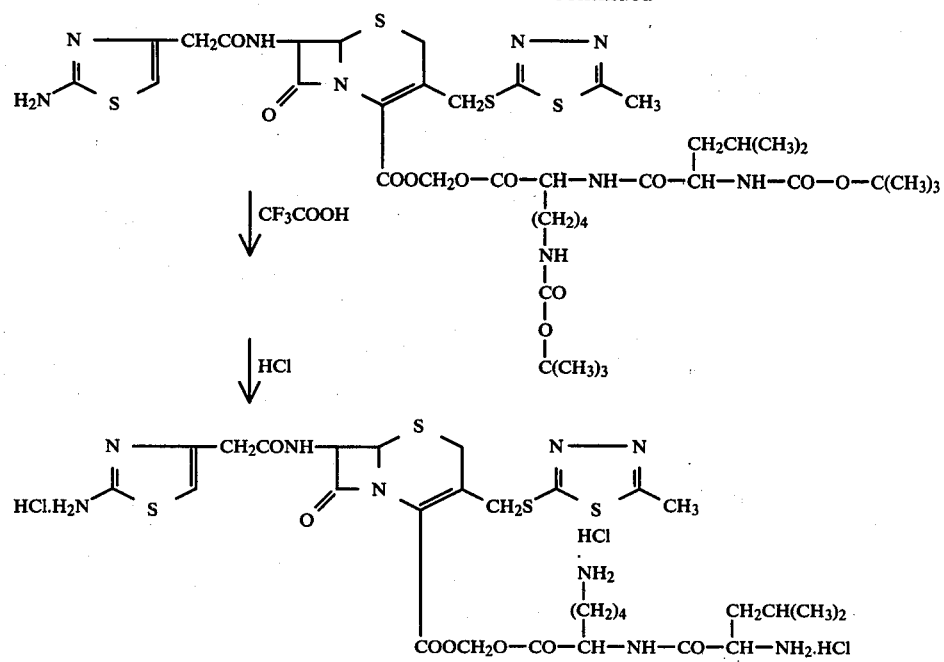

In 30 ml of N,N-dimethylformamide were dissolved 2.0 g of α-tert-butyloxycarbonyl-L-leucyl-ε-tert-butyloxycarbonyl-L-lysine and 0.45 g of triethylamine. To the solution was added 0.77 g of chloroiodomethane and the mixture was stirred at 20° C. for 25 hours. Then, most N,N-dimethylformamide was removed under reduced pressure and to the residue thus obtained was added 50 ml of mixture consisting of ethyl acetate and water in a volume ratio of 1:1. After shaking the mixed solution well, the ethyl acetate layer was washed with 5% aqueous sodium hydrogencarbonate solution and dried with anhydrous magnesium sulfate. Then the ethyl acetate was removed under reduced pressure and the residue thus obtained was subjected to silica gel chromatography to separate 2.1 g of (α-tert-butyloxycarbonyl-L-leucyl-ε-tert-butyloxycarbonyl-L-lysyl)-chloromethyl ester.

To 40 ml of an acetone solution containing 2.1 g of (α-tert-butyloxycarbonyl-L-leucyl-ε-tert-butyloxycarbonyl-L-lysyl)chloromethyl ester was added 1.2 g of sodium iodide and the mixture was stirred in a nitrogen gas atmosphere for 17 hours to separate sodium chloride. The sodium chloride was removed by filtration and the filtrate was concentrated under reduced pressure. The residue thus obtained was dissolved in ether and insolubles were removed by filtration. After removing the ether from the filtrate, in 20 ml of N,N-dimethylformamide was dissolved the filtrate. Then the solution was added to 40 ml of a N,N-dimethylformamide solution containing 2.0 g of sodium 7-[2-(2-amino-4-thiazolyl)acetoamido-3-(5-methyl-1,3,4-thiadiazolyl)-thiomethyl]-3-cepehm-4-carboxylate and the reaction was carried out at 20° C. for 15 minutes. After completion of the reaction, part of N,N-dimethylformamide was removed, and to the reaction mixture were added 100 ml of water and ethyl acetate as the extraction liquid. The ethyl acetate layer was washed with a 1N aqueous hydrochloric acid solution, a 10% aqueous sodium hydrogencarbonate solution and a saturated sodium chloride solution, and dried with anhydrous magnesium sulfate. Then the ethyl acetate was removed from the layer to give solid residue.

The residue thus obtained was added to 30 ml of trifluoroacetic acid and the reaction was carried out at 0° C. with stirring for 20 minutes. After completion of the reaction, excess trifluoroacetic acid was removed under reduced pressure. The residue thus obtained was dissolved in ethyl acetate and the solution was washed twice with an aqueous sodium hydrogencarbonate solution and then twice with a saturated sodium chloride solution. The ethyl acetate layer was dried with anhydrous magnesium sulfate and added with ether saturated with anhydrous hydrogen chloride. The solvents were removed under reduced pressure to give 0.8 g of a compound.

The compound thus obtained was identified as 7-[2-(2-amino-4-thiazolyl)acetoamido-3-(5-methyl-1,3,4-thiadiazolyl)-thiomethyl]-3-cephem-4-carboxylic acid L-leucyl-L-lysyloxymethyl ester hydrochloric acid salt by the following NMR spectrum of the compound.

| | | |
|---|---|---|
| 0.83 ppm | $CH_3$<br>    $\diagdown$<br>       CH—<br>    $\diagup$<br>$CH_3$ | doublet |
| 1.40 ppm | $CH_3$<br>    $\diagdown$<br>       CH—$CH_2$—<br>    $\diagup$<br>$CH_3$ | multiplet |
| 2.63 ppm | N——N<br>   ∥     ∥<br>—$CH_2S$  S  $CH_3$ | singlet |
| 1.77 ppm | —CH—<br>    \|<br>  ($CH_2$)$_3$<br>    \|<br>  $CH_2$<br>    \|<br>  $NH_2$ | multiplet |

| ppm | group | multiplicity |
|---|---|---|
| 3.65 ppm | N—CH₂— with H₂N-C(=)-S ring (2-aminothiazolyl-CH₂) | multiplet |
| 3.70 ppm | cephem ring S-CH₂, β-lactam structure | multiplet |
| 4.33 ppm | —CH₂S—(thiadiazole)—CH₃ | multiplet |
| 5.02 ppm | O=C—CH(NH—)—(CH₂)₄—NH₂ (lysine side chain) | multiplet |
| 5.10 ppm | 6-H | doublet |
| 5.65 ppm | 7-H | multiplet |
| 6.90 ppm | 2-aminothiazolyl =CH— | singlet |
| 8.93 ppm | H₂N-C(=N)-S thiazolyl-CH₂CONH— | multiplet |

The absorption test results of 7-[2-(2-amino-4-thiazolyl)-acetoamido-3-(5-methyl-1,3,4-thiadiazolyl)-thiomethyl]-3-cephem-4-carboxylic acid L-leucyl-L-lysyloxymethyl ester hydrochloric acid salt are as follows:

|  | 0.5 hr. | 1 hr. | 2 hrs. | 4 hrs. |
|---|---|---|---|---|
| Blood Concentration of Compound (III)* (μg/ml) | 1.96 | 2.37 | 1.03 | 0.24 |

EXAMPLES 16–18

The same procedures as desribed in Example 15 were repeated except that other oligopeptides were employed instead of the α-tert-butyloxycarbonyl-L-leucyl-ε-tert-butyloxycarbonyl-L-lysine. As a result, the cephalosporin derivatives having the oligopeptides as set forth in Table 3 were obtained. The absorption test results of the compounds thus obtained are shown in Table 3.

TABLE 3

| Example No. | Oligopeptide | | | Blood Concentration of Compound (III) (μg/ml) | | | |
|---|---|---|---|---|---|---|---|
|  | X | Amino Acid Unit Containing $R_1$ | Amino Acid Unit Containing $R_2$ | n | 0.5 hr | 1 hr | 2 hrs | 4 hrs |
| 16 | H | Gly | Lys | 1 | 1.48 | 1.06 | 0.34 | <0.1 |
| 17 | H | Met | Leu | 3 | 0.15 | 0.23 | 0.16 | <0.1 |
| 18 | H | Cys(D) | Phe | 1 | 0.23 | 0.54 | <0.1 | <0.1 |
| Comparative | | (none) | | | <0.1 | <0.1 | <0.1 | <0.1 |

Note:
(1) (D) shows the D-isomer of the amino acid. Amino acids without the indication show the L-isomers.
(2) In Comparative Example Compound (III) was employed in the absorption test.

EXAMPLE 19

7β-(2-L-phenylalanyl-L-leucylamidoethylthioacetoamido)-3-acetoxymethyl-3-cephem-4-carboxylic acid trifluoroacetic acid salt was prepared in accordance with the following equations:

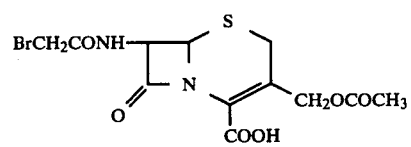

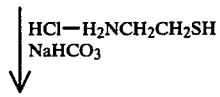

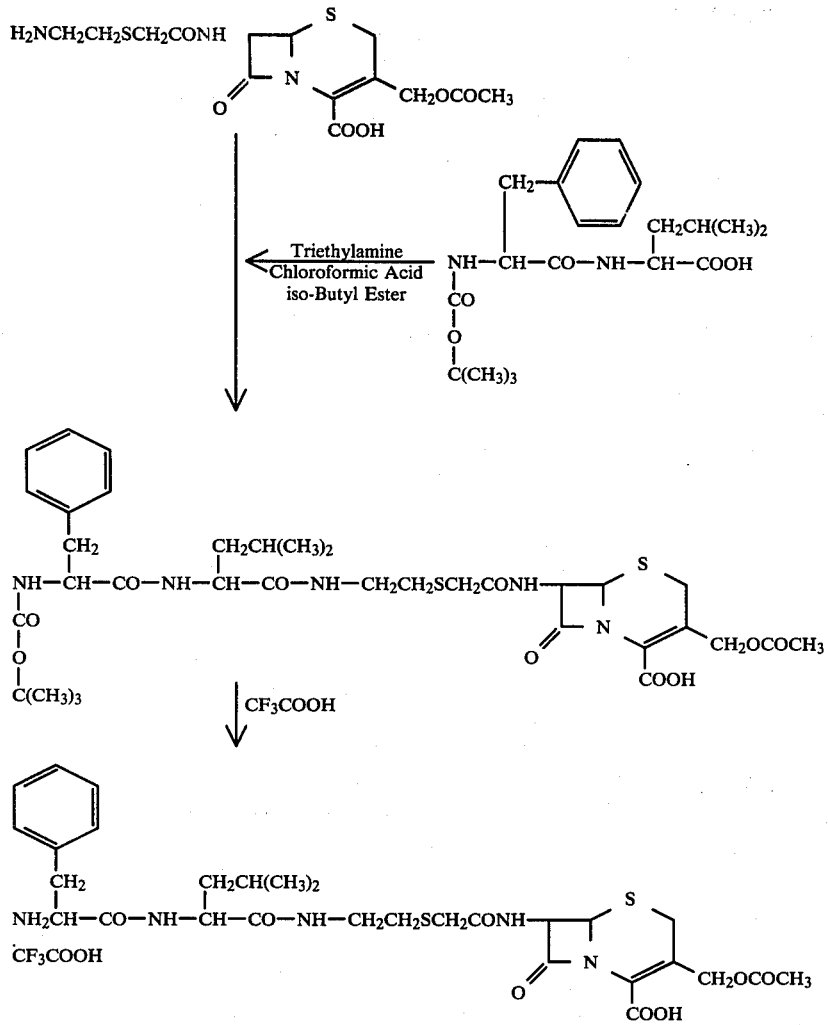

To 30 ml of water was added 2 g of 7β-bromoacetoamidocephalosporanic acid, and the pH of the solution was adjusted to 7 with sodium hydrogencarbonate. To the solution was added 0.76 g of mercaptoethylamine hydrochloric acid salt and the reaction was carried out at 0° C. for 2 hours while maintaining the pH of the reaction solution at 7. After the pH of the reaction solution was adjusted to 5 with hydrochloric acid, the solution was passed through a column packed with XAD-II (product of Japan Organo Co., Ltd.) and the column was washed with water. Then a mixed solvent of water and acetone was passed through the column to elute 1.1 g of 7β-(aminoethylthioacetoamido)-3-acetoxymethyl-3-cephem-4-carboxylic acid (Compound IV).

To 30 lm of tetrahydrofuran were added 1.0 g of 60-tert-butyloxycarbonyl-L-phenylalanyl-L-leucine and 0.3 g of triethylamine and the mixture was stirred for 20° C. for 10 minutes. To the mixture was added 0.4 g of chloroformic acid iso-butyl ester at −10° C. and the mixture obtained was stirred for 30 minutes. Then to the mixture was added 1.1 g of 7β-(aminoethylthioacetoamido)-3-acetoxymethyl-3-cephem-4-carboxylic acid, and the reaction was carried out at −10° C. with stirring for one hour. After completion of the reaction, the reaction mixture was slightly acidified with 1N hydrochloric acid, and the solvent was removed under reduced pressure from the reaction mixture. To the residue thus obtained was added 100 ml of a mixture consisting of ethyl acetate and water in a volume ratio of 1:1. After thoroughly shaking the mixed solution the ethyl acetate layer was washed with water and dried with anhydrous sodium sulfate. The ethyl acetate was removed to give 7β-(tert-butyloxycarbonyl-L-phenylalanyl-L-leucylamidoethylthioacetoamido)-3-acetoxymethyl-3-cephem-4-carboxylic acid.

To 30 ml of trifluoroacetic acid was added 7β-(tert-butyloxycarbonyl-L-phenylalanyl-L-leucylamidoethylthioacetoamido)-3-acetoxymethyl-3-cephem-4-carboxylic acid and the reaction was carried out at 0° C. with stirring for 15 minutes. After completion of the reaction, excess trifluoroacetic acid was removed under reduced pressure. To the residue thus obtained was added 50 ml of ethyl ether with stirring to precipitate the crystals. The crystals were separated by filtration. The amount of the crystals was 1.2 g.

The precipitates was identified as the 7β-(2-L-phenylalanyl-L-leucylamidoethylthioacetoamido)-3-acetoxymethyl-3-cephem-4-carboxylic acid trifluoroacetic acid salt by the following NMR spectrum of the precipitates.

NMR Spectrum(in DMSO):

| | | |
|---|---|---|
| 0.82 ppm | CH₃\\CH—/CH₃ | doublet |
| 1.21 ppm | CH₃\\CH—CH₂—/CH₃ | multiplet |
| 2.00 ppm | —CH₂OCOCH₃ | singlet |
| 3.02 ppm | C₆H₅—CH₂— | multiplet |
| 3.30 ppm | —NH—CH₂—CH₂— | multiplet |
| 3.90 ppm | —S—CH₂—CO— | singlet |
| 4.80 ppm | —CH₂OCOCH₃ | multiplet |
| 5.00 ppm | 6-H | doublet |
| 5.60 ppm | 7-H | multiplet |
| 7.28 ppm |  | multiplet |

The absorption test results of 7β-(2-L-phenylalanyl-L-leucylamidoethylthioacetoamido)-3-acetoxymethyl-3-cephem-4-carboxylic acid trifluoroacetic acid salt are as follows:

| | 0.5 hr. | 1 hr. | 2 hrs. | 4 hrs. |
|---|---|---|---|---|
| Blood Concentration of Compound (IV) (μg/ml) | 1.07 | 0.21 | 0.09 | <0.01 |

EXAMPLES 20-21

The same procedures as described in Example 19 were repeated except that other oligopeptides were employed instead of the tert-butyloxycarbonyl-L-phenylalanyl-L-leucine. As a result, the cephalosporin derivatives having the oligopeptides as set forth in Table 4 were obtained. The absorption test results of the compounds thus obtained are shown in Table 4.

TABLE 4

| Example No. | Oligopeptide | | | Blood Concentration of Compound (IV) (μg/ml) | | | |
|---|---|---|---|---|---|---|---|
| | X | Amino Acid Unit Containing R₁ | Amino Acid Unit Containing R₂ | n | 0.5 hr | 1 hr | 2 hrs | 4 hrs |
| 20 | H | Ala | Leu | 1 | 1.01 | 0.32 | 0.10 | <0.01 |
| 21 | H | Ala | Leu (D) | 1 | 0.14 | 0.32 | 0.05 | <0.01 |
| Comparative | | (None) | | | 0.09 | 0.06 | <0.01 | <0.01 |

Note:
(1) (D) shows the D-isomer of the amino acid. The amino acid without the indication shows the L-isomer.
(2) In Comparative Example Compound (IV) was employed in the absorption test.

EXAMPLE 22

7β-[2-(2-L-leucyl-L-phenylalanylamidothiazol-4-yl)-(Z)-2-methoxyiminoacetoamido]cephalosporanic acid formic acid salt was prepared in accordance with the following equations:

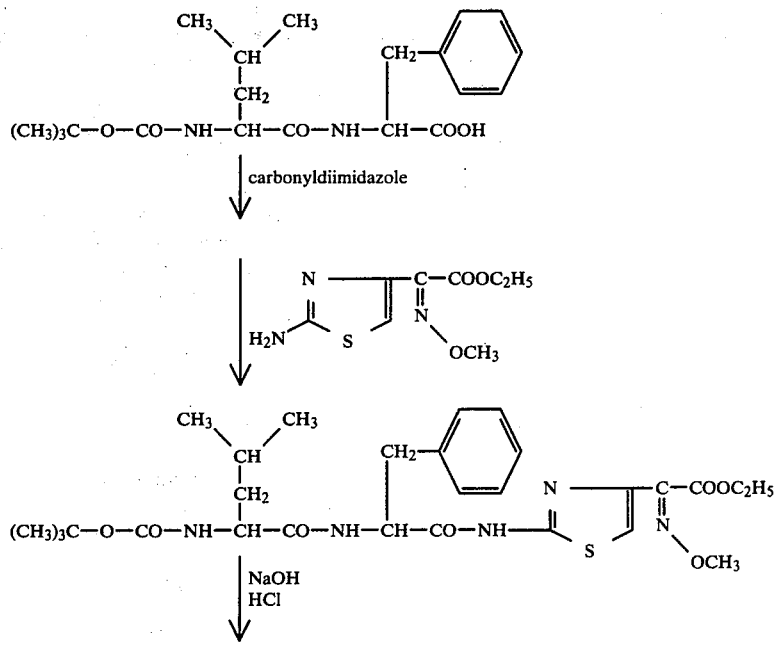

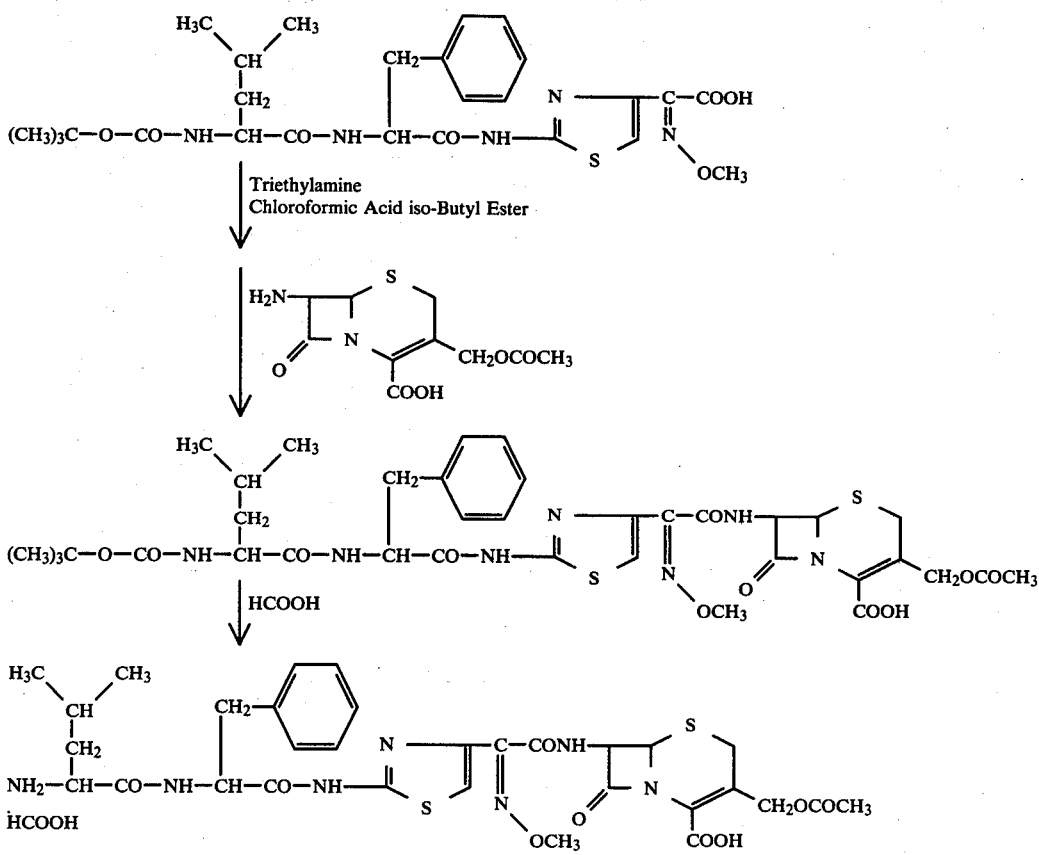

In 20 ml of anhydrous tetrahydrofuran was dissolved 1.52 g of tert-butyloxycarbonyl-L-leucyl-L-phenylalanine and to the solution was added 0.64 g of N,N'-carbonyldiimidazole and the reaction was carried out at 10°–25° C. with stirring for 30 minutes. To the reaction mixture was added 10 ml of a tetrahydrofuran solution containing 1.34 g of 2-(2-aminothiazol-4-yl)-(Z)-2-methoxyiminoacetic acid ethyl ester p-toluenesulfonic acid salt and 0.4 g of triethylamine and the reaction was carried out at 10°–25° C. for 20 hours. After completion of the reaction, tetrahydrofuran was removed under reduced pressure. The residue was dissolved in 30 ml of ethyl acetate and the solution was washed twice with 30 ml of 1N hydrochloric acid. Then the solution was further washed with a 5% aqueous sodium hydrogencarbonate solution and then with water. The ethyl acetate layer was dried with anhydrous sodium sulfate and then ethyl acetate was removed under reduced pressure to give crude crystals of 2-(2-tert-butyloxycarbonyl-L-leucyl-L-phenylalanylamidothiazol-4-yl)-(Z)-2-methoxyiminoacetic acid ethyl ester.

In 30 ml of ethyl alcohol were dissolved the crude crystals thus obtained and to the solution was added equivalent sodium hydroxide to the crystals. The reaction was carried out 15°–25° C. for one hour. After completion of the reaction, the ethyl alcohol was removed and to the residue thus obtained was added 20 ml of water. The pH of the solution was adjusted to 2–3 by adding 1N hydrochloric acid under cooling with ice to separate crystals of 2-(2-tert-butyloxycarbonyl-L-leucyl-L-phenylalanylamidothiazol-4-yl)-(Z)-2-methoxyiminoacetic acid. In 30 ml of tetrahydrofuran were dissolved 1.4 g of the crystals thus obtained and the solution was cooled at −10° C. To the solution were added 0.3 g of triethylamine and 0.4 g of chloroformic acid iso-butyl ester and the reaction was carried out at −10° C. for one hour. To the reaction solution were added 0.9 g of 7-aminocephalosporanic acid and 0.4 g of triethylamine which were dissolved in 20 ml of a 50% aqueous tetrahydrofuran solution and the reaction was carried out at 0°–5° C. for 2 hours. After completion of the reaction, tetrahydrofuran was removed under reduced pressure. The residue thus obtained was dissolved in 100 ml of water and the solution was washed with 20 ml of ethyl acetate. After the pH of the aqueous solution was adjusted to 2–3 with 1N hydrochloric acid, ethyl acetate was added to the solution. The ethyl acetate layer was washed with water and dried with anhydrous sodium sulfate. Then the ethyl acetate was removed from the layer to give crude crystals. The crude crystals were subjected to column chromatography packed with XAD-II (product of Japan Organo Co., Ltd.) for the purification and 1.3 g of crystals were obtained.

The purified crystals thus obtained were dissolved in 20 ml of formic acid at 10°–20° C. and the reaction was carried out with stirring the solution for one hour. After completion of the reaction, the formic acid was removed under reduced pressure, and to the residue thus obtained was added 20 ml of ether to separate the crystals.

The compound thus obtained was identified as 7β-[2-(2-L-leucyl-L-phenylalanylamidothiazol-4-yl)-(Z)-2-methoxyiminoacetoamido]cephalosporanic acid formic acid salt by the following NMR spectrum of the compound. The NMR was measured after the sodium salt of the compound was prepared.

NMR Spectrum (in D₂O):

| | | |
|---|---|---|
| 0.85 ppm | (CH₃)₂CH— | doublet |
| 1.40 ppm | (CH₃)₂CH—CH₂— | multiplet |
| 2.03 ppm | —COCH₃ | singlet |
| 3.20 ppm | C₆H₅—CH₂— | multiplet |
| 3.50 ppm | β-lactam S, CH₂ | multiplet |
| 4.00 ppm | —C=N—OCH₃ | singlet |
| 4.79 ppm | —CH₂OCOCH₃ | multiplet |
| 5.18 ppm | 6-H | doublet |
| 5.79 ppm | 7-H | doublet |
| 7.43 ppm | thiazole-H | singlet |
| 7.20 ppm | C₆H₅— | multiplet |

The absorption test results of 7β-[2-(2-L-leucyl-L-phenylalanylamidothiazol-4-yl)-(Z)-2-methoxyiminoacetoamido]cephalosporanic acid are shown in Table 5.

EXAMPLES 23–24

The same procedures as described in Example 22 were repeated except that other oligopeptides were employed instead of the tert-butyloxycarbonyl-L-leucyl-L-phenylalanine. As a result, the cephalosporin derivatives having the oligopeptides as set forth in Table 5 were obtained. The absorption test results of the compounds thus obtained are shown in Table 5.

TABLE 5

| Example No. | Oligopeptide | | | | Blood Concentration of Compound (V) (μg/ml) | | | |
|---|---|---|---|---|---|---|---|---|
| | X | Amino Acid Unit Containing R₁ | Amino Acid Unit Containing R₂ | n | 0.5 hr. | 1 hr. | 2 hrs. | 4 hrs. |
| 22 | H | Leu | Phe | 1 | 1.69 | 1.83 | 1.53 | 1.03 |
| 23 | HCO | Ile | Met | 1 | 0.24 | 0.20 | <0.1 | <0.1 |
| 24 | H | Asp | Phe | 1 | 0.65 | 0.81 | 0.31 | <0.1 |
| Comparative | (None) | | | | <0.1 | <0.1 | <0.1 | <0.1 |

Note:
¹The chemical formula of Compound (V) is as follows:

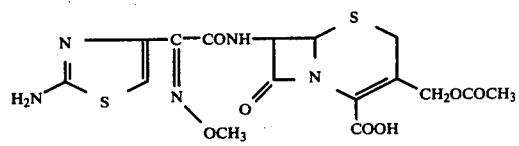

²All the amino acids were the L-isomers.
³In Comparative Example Compound (V) was employed in the absorption test.

EXAMPLE 25

7β-[2-(2-L-leucyl-L-lysylamidothiazol-4-yl)-(Z)-2-methoxyiminoacetoamido]-3-[(1-methyl-1H-tetrazol-5-yl)-thiomethyl]-3-cephem-4-carboxylic acid formic acid salt was prepared in accordance with the following equations:

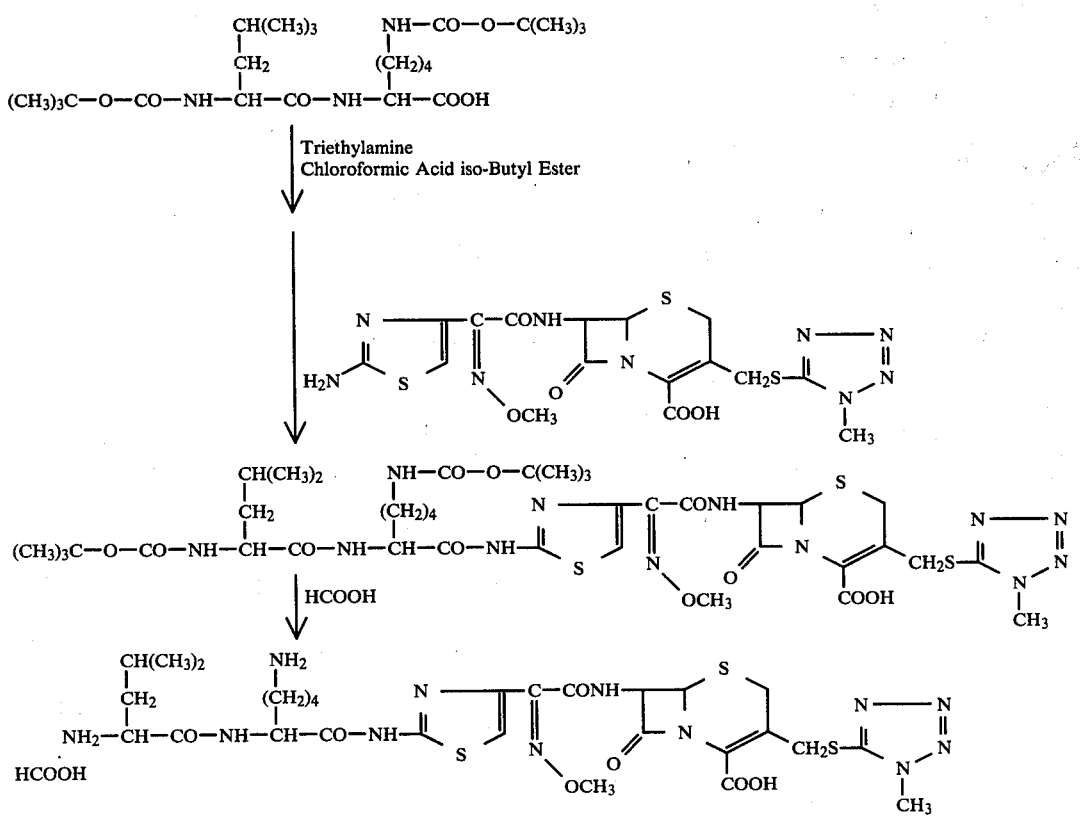

To 30 ml of tetrahydrofuran was added 2.0 g of α-tert-butyloxycarbonyl-L-leucyl-ε-tert-butyloxycarbonyl-L-lysine and 0.45 g of triethylamine and to the mixture was added 0.66 g of chloroformic acid isobutyl ester under cooling with ice. After the reaction was carried out for 10 minutes, to the reaction mixture were added 2.8 g of 7β-[2-(2-aminothiazol-4-yl)-(Z)-2-methoxyiminoacetoamido]-3-[(1-methyl-1H-tetrazol-5-yl)-thiomethyl]-3-cephem-4-carboxylic acid [Compound (VI)] and 0.56 g of triethylamine which were dissolved in 10 ml of water at 2°–5° C. and the reaction was carried out for 30 minutes. After completion of the reaction, the pH of the reaction mixture was adjusted to 2-3 with 1N hydrochloric acid. Tetrahydrofuran was removed under reduced pressure from the reaction mixture to separate crystals. The crystals thus obtained were subjected to column chromatography packed with XAD-II (product of Japan Organo Co., Ltd.) for the purification.

In 30 ml of formic acid were dissolved 2.3 g of the purified crystals and the reaction was carried out at 10°–20° C. for one hour. After completion of the reaction, the formic acid was removed under reduced pressure. To the residue thus obtained was added 20 ml of ether to separate crystals.

The compound thus obtained was identified as 7β-[2-(2-L-leucyl-L-lysylamidothiazol-4-yl)-(Z)-2-methoxyiminoacetoamido]-3-[1-methyl-1H-tetrazol-5-yl)-thiomethyl]-3-cephem-4-carboxylic acid formic acid salt by the following NMR spectrum of the compound. The NMR was measured after the sodium salt of the compound was prepared.

NMR Spectrum (in D$_2$O):

-continued

| | | |
|---|---|---|
| 5.03 ppm | O<br>‖<br>—C—CH—NH—<br>　　｜<br>　　(CH$_2$)$_4$—NH$_2$ | multiplet |
| 5.14 ppm | 6-H | doublet |
| 5.72 ppm | 7-H | doublet |
| 7.40 ppm | $\begin{array}{c} N \underline{\hspace{1em}} \\ -HN\diagdown_S\diagup^H \end{array}$ | singlet |

The absorption test results of 7β-[2-(2-L-leucyl-L-lysylamidothiazol-4-yl)-(Z)-2-methoxyiminoacetoamido]-3-[1-methyl-1H-tetrazol-5-yl)-thi-omethyl]-3-cephem-4-carboxylic acid are shown in Table 6.

EXAMPLE 26

The same procedures as described in Example 25 were repeated except that another oligopeptide was employed instead of the α-tert-butyloxycarbonyl-L-Leucyl-ε-tert-butyloxycarbonyl-L-lysine. As a result, the cephalosporin derivative having the oligopeptide as set forth in Table 6 was obtained. The absorption test results of the compound thus obtained are shown in Table 6.

TABLE 6

| Example No. | Oligopeptide | | | | Blood Concentration of Compound (VI) (μg/ml) | | | |
|---|---|---|---|---|---|---|---|---|
| | X | Amino Acid Unit Containing R$_1$ | Amino Acid Unit Containing R$_2$ | n | 0.5 hr | 1 hr | 2 hrs. | 4 hrs. |
| 25 | H | Leu | Lys | 1 | 2.11 | 1.67 | 1.10 | <0.1 |
| 26 | H | Tyr | Phe | 1 | 1.24 | 1.33 | 0.74 | <0.1 |
| Comparative | (None) | | | | <0.1 | <0.1 | <0.1 | <0.1 |

Note:
(1) Tyr and Phe were the L-isomers.
(2) In Comparative Example Compound (VI) was employed in the absorption test.

EXAMPLE 27

7β-[2-(2-L-methionyl-L-phenylalanylamidothiazol-4-yl)-(Z)-2-methoxyiminoacetamido]-3-cephem-4-carboxylic acid formic acid salt was prepared in accordance with the following equations:

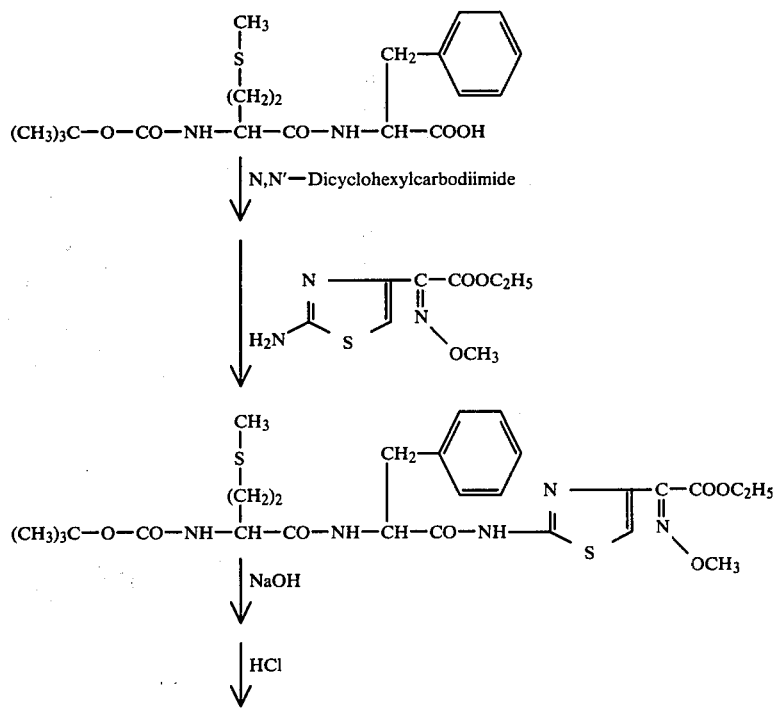

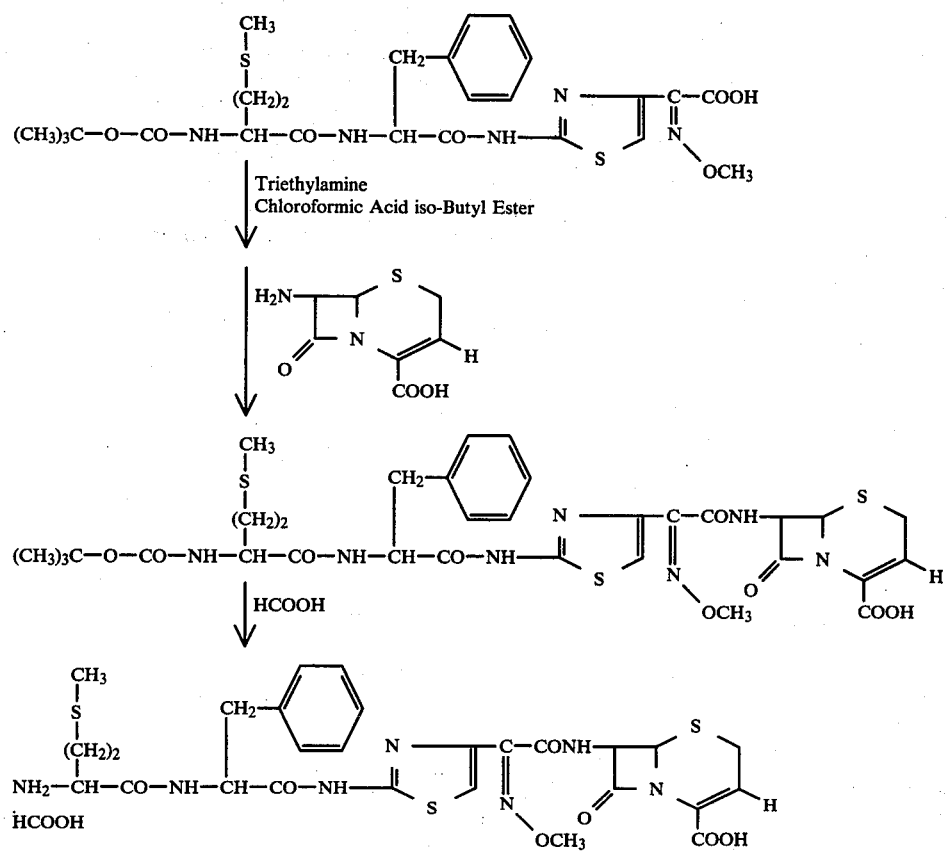

In 25 ml of anhydrous tetrahydrofuran were dissolved 2 g of tert-butyloxycarbonyl-L-methionyl-L-phenylalanine and 1.1 g of N,N'-dicyclohexylcarbodiimide and the reaction was carried out at 15°–20° C. with stirring for 30 minutes. To the reaction solution was added 1.20 g of 2-(2-aminothiazol-4-yl)-(Z)-2-methoxyiminoacetic acid ethyl ester and the reaction was carried out at 20° C. for 30 hours. After completion of the reaction, tetrahydrofuran was removed under reduced pressure. The residue thus obtained was dissolved in 30 ml of ethyl acetate and insolubles were removed. The ethyl acetate solution was subjected to column chromatography packed with XAD-II (product of Japan Organo Co., Ltd.) for the purification and as a result, the crystals of 2-(2-tert-butyloxycarbonyl-L-methyonyl-L-phenylalanylamidothiazol-4-yl)-(Z)-2-methoxyiminoacetic acid ethyl ester were obtained.

The crystals thus obtained were dissolved in 30 ml of ethyl alcohol and to the solution was added equivalent sodium hydroxide to the crystals and the reaction was carried out at 20° C. for one hour. After completion of the reaction, the ethyl alcohol was removed. To the residue thus obtained was added 20 ml of water and the pH of the solution was adjusted to 2–3 by adding 1N hydrochloric acid under cooling with ice to separate crystals. Then, 1.4 g of the crystals thus obtained was dissolved in 35 ml of tetrahydrofuran and the solution was cooled to 0° C. To the solution were added 0.30 g of triethylamine and 0.38 g of chloroformic acid iso-butyl ester and the reaction was carried out at 0° C. for 10 minutes. Then, to the solution were added 0.61 g of 7-amino-3-cephem-4-carboxylic acid and 0.34 g of triethylamine which were dissolved in 20 ml of a 50% aqueous tetrahydrofuran solution and the reaction was carried out at 0°–5° C. for one hour. After completion of the reaction, the tetrahydrofuran was removed under reduced pressure and the residue thus obtained was dissolved in 100 ml of water. The aqueous solution was washed twice with 20 ml of ethyl acetate. After the pH of the aqueous solution was adjusted with 1N hydrochloric acid, to the solution was added ethyl acetate as the extraction liquid. The ethyl acetate layer was washed with water and dried with anhydrous sodium sulfate. Then, the ethyl acetate was removed from the layer to give crude crystals. The crude crystals were purified by column chromatography packed with XAD-II (product of Japan Organo Co., Ltd.) to give 0.9 g of crystals.

The crystals thus obtained were dissolved in 20 ml of formic acid at 10°–20° C., and the reaction was carried out with stirring for one hour. After completion of the reaction, the formic acid was removed under reduced pressure, and to the residue thus obtained was added 20 ml of ether to separate crystals.

The compound thus obtained was identified as 7β-[2-(2-L-methionyl-L-phenylalanylamidothiazol-4-yl)-(Z)-2-methoxyiminoacetoamido]-3-cephem-4-carboxylic acid formic acid salt by the following NMR spectrum of the compound. The NMR was measured after the sodium salt of the compound was prepared.

NMR Spectrum (in $D_2O$):

| 2.15 ppm | $CH_3$—S— | singlet |

-continued

| | | |
|---|---|---|
| 3.20 ppm | ⟨phenyl⟩–CH₂– | multiplet |
| 3.60 ppm | (β-lactam with S, COOH, =CH-H structure) | multiplet |
| 3.97 ppm | –C(=N–OCH₃)– | singlet |
| 5.21 ppm | 6-H | doublet |
| 5.87 ppm | 7-H | doublet |
| 6.33 ppm | (β-lactam with S, COOH, =CH-H structure) | multiplet |
| 7.46 ppm | (thiazole N=C(–)–S–C(H)=) | singlet |

-continued

| | | |
|---|---|---|
| 7.18 ppm | H-substituted benzene–CH₂– | multiplet |

The absorption test results of 7β-[2-(2-L-methionyl-L-phenylalanylamidothiazol-4-yl)-(Z)-2-methoxyiminoacetoamido]-3-cephem-4-carboxylic acid are shown in Table 7.

EXAMPLE 28

The same procedures as described in Example 27 were repeated except that another oligopeptide was employed instead of the tert-butyloxycarbonyl-L-methionyl-L-phenylalanine. As a result, the cephalosporin derivative having the oligopeptide as set forth in Table 7 was obtained. The absorption test results of the compound thus obtained are shown in Table 7.

TABLE 7

| Example No. | Oligopeptide X | Amino Acid Unit Containing $R_1$ | Amino Acid Unit Containing $R_2$ | n | Blood Concentration of Compound (VII) (μg/ml) 0.5 hr | 1 hr | 2 hrs. | 4 hrs. |
|---|---|---|---|---|---|---|---|---|
| 27 | H | Met | Phe | 1 | 2.13 | 1.84 | 1.00 | 0.21 |
| 28 | H | His | Phe | 1 | 1.84 | 1.77 | 1.01 | 0.24 |
| Comparative | | (None) | | | <0.1 | <0.1 | <0.1 | <0.1 |

Note:
(1) The chemical formula of Compound (VII) is as follows:

$$H_2N-C(S)=N-C(=N-OCH_3)-CONH-[\beta\text{-lactam}]-N=CH-COOH$$

(2) His and Phe used in Example 28 were the L-isomers.
(3) In comparative Example Compound (VII) was employed in the absorption test.

EXAMPLE 29

7β-[(cyanomethyl)thio]acetoamido-7α-methoxy-3-[(1-methyl-1H-tetrazol-5-yl)thio]methyl-3-cephem-4-carboxylic acid L-leucyl-L-lysyloxymethyl ester hydrochloric acid salt was prepared in accordance with the following equations:

(CH₃)₃C—O—CO—NH—CH(CH₂CH(CH₃)₂)—CO—NH—CH((CH₂)₄—NH—CO—O—C(CH₃)₃)—CO—OH

↓ Triethylamine
↓ ICH₂Cl (CH₃)₃C—O—CO—NH—CH(CH₂CH(CH₃)₂)—CO—NH—CH((CH₂)₄—NH—CO—O—C(CH₃)₃)—CO—OCH₂Cl

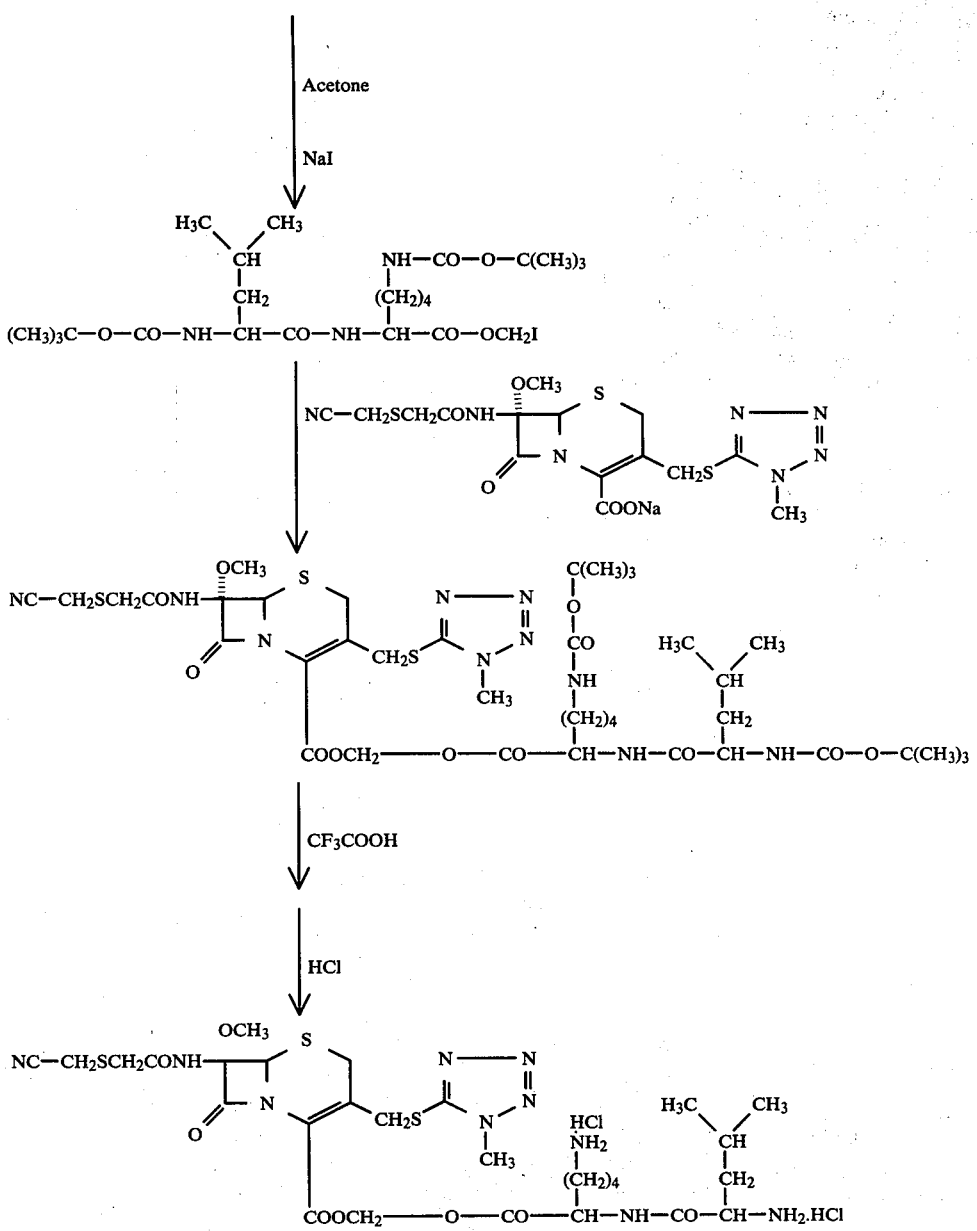

In 30 m of N,N-dimethylformamide were dissolved 2.0 g of α-tert-butyloxycarbonyl-L-leucyl-ε-tert-butyloxycarbonyl-L-lysine and 0.45 g of triethylamine. To the solution was added 0.77 g of chloroiodomethane and the mixture was stirred at 20° C. for 25 hours. Most N,N-dimethylformamide was removed under reduced pressure and to the residue thus obtained was added 50 ml of a mixed liquid consisting of ethyl acetate and water in a volume ratio of 1:1. After thoroughly shaking the mixed solution, the ethyl acetate layer was washed with a 5% aqueous sodium hydrogencarbonate solution and dried with anhydrous magnesium sulfate. Then the ethyl acetate was removed under reduced pressure and the residue thus obtained was subjected to silica gel chromatography to separate 2.0 g of (α-tert-butyloxycarbonyl-L-leucyl-ε-tert-butyloxycarbonyl-L-lysyl)-chloromethyl ester.

To 40 ml of an acetone solution containing 2.0 g of (α-tert-butyloxycarbonyl-L-leucyl-ε-tert-butyloxycarbonyl-L-lysyl)chloromethyl ester was added 1.2 g of sodium iodide, and the reaction was carried out with stirring in a nitrogen gas atmosphere for 17 hours to separate sodium chloride. The sodium chloride was removed by filtration, and the filtrate was concentrated under reduced pressure. The residue thus obtained was dissolved in ether and insolubles were removed by filtration. After removing the ether from the filtrate, the filtrate was dissolved in 20 ml of N,N-dimethylformamide. The solution obtained was added to 40 ml of a N,N-dimethylformamide solution containing 2.3 g of sodium 7β-[(cyanomethyl)thio]acetoamido-7α-methoxy-3-[(1-methyl-1H-tetrazol-5-yl)thio]methyl-3-cephem-4-carboxylate and the reaction was carried out at 20° C. for 60 minutes. After completion of the reaction, part of the N,N-dimethylformamide was removed and to the reaction mixture was added 100 ml of water and ethyl acetate as the extraction liquid. The ethyl acetate layer was washed with a 1N aqueous hydrochloric acid solution, a 10% aqueous sodium hydrogencarbonate solution and a saturated sodium chloride solution, and dried with anhydrous magnesium sulfate. Then, the ethyl acetate was removed from the layer to give solid residue.

The residue thus obtained was added to 30 ml of trifluoroacetic acid and the reaction was carried out at 0° C. with stirring for 25 minutes. After completion of the reaction, excess trifluoroacetic acid was removed under reduced pressure. The residue thus obtained was dissolved in ethyl acetate and the solution was washed twice with an aqueous sodium hydrogencarbonate solution and then twice with a saturated sodium chloride solution. The ethyl acetate layer was dried with anhydrous magnesium sulfate and added with ether saturated with anhydrous hydrogen chloride. The solvents were removed under reduced pressure to give 1.3 g of a compound.

The compound was identified as 7β-[(cyanomethyl)-thio]acetoamido-7α-methoxy-3-[(1-methyl-1H-tetrazol-5-yl)thio]methyl-3-cephem-4-carboxylic acid L-leucyl-L-lysyloxymethyl ester hydrochloric acid salt by the following NMR spectrum of the compound.

NMR spectrum in (D$_2$O):

| | | |
|---|---|---|
| 0.83 ppm | CH$_3$\<br>　　＼<br>　　　CH—<br>　　／<br>CH$_3$ | doublet |
| 1.40 ppm | CH$_3$\<br>　　＼<br>　　　CH—CH$_2$—<br>　　／<br>CH$_3$ | multiplet |
| 1.76 ppm | ＼<br>　CH—(CH$_2$)$_3$—CH$_2$—NH$_2$<br>／ | multiplet |
| 3.50~3.82 ppm | 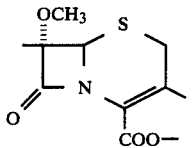 | multiplet |
| 3.62 ppm | 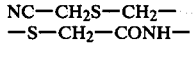 | singlet |
| 3.70 ppm<br>3.75 ppm | NC—CH$_2$S—CH$_2$—<br>—S—CH$_2$—CONH— | singlet<br>singlet |
| 4.08 ppm | 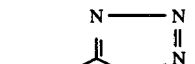 | singlet |
| 4.20~4.40 ppm | 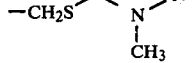 | multiplet |
| 5.24 ppm | 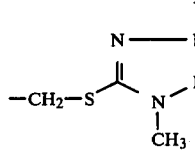 | singlet |

The absorption test results of 7β-[(cyanomethyl)thio]acetoamido-7α-methoxy-3-[(1-methyl-1H-tetrazol-5-yl)thio]methyl-3-cephem-4-carboxylic acid L-leucyl-L-lysyloxymethyl ester hydrochloric acid salt are shown in Table 8.

EXAMPLES 30–34

The same procedures are described in Example 29 were repeated except that other oligopeptides were employed instead of the α-tert-butyloxycarbonyl-L-leucyl-ε-tert-butyloxycarbonyl-L-lysine. As a result, the cephalosporin derivatives having the oligopeptides as set forth in Table 8 were obtained. The absorption test results of these compounds are shown in Table 8.

TABLE 8

| Example No. | Oligopeptide | | | Blood Concentration of Compound (VIII) (μg/ml) | | | |
|---|---|---|---|---|---|---|---|
| | X | Amino Acid Unit Containing R$_1$ | Amino Acid Unit Containing R$_2$ | n | 0.5 hr | 1 hr | 2 hrs. | 4 hrs. |
| 29 | H | Leu | Lys | 1 | 3.14 | 2.37 | 1.04 | 0.32 |
| 30 | H | Val | Lys | 1 | 1.24 | 0.84 | 0.31 | <0.1 |
| 31 | H | Arg | Phe | 1 | 1.03 | 1.01 | 0.42 | 0.24 |
| 32 | H | Ser | Phe | 1 | 0.86 | 0.42 | 0.14 | <0.1 |
| 33 | HCO | Leu | Orn | 1 | 0.41 | 0.23 | <0.1 | <0.1 |
| 34 | H | α-ABA | Phe | 1 | 0.30 | 0.12 | <0.1 | <0.1 |
| Comparative | | (None) | | | <0.1 | <0.1 | <0.1 | <0.1 |

Note:
(1) The chemical formula of Compound (VIII) is as follows:

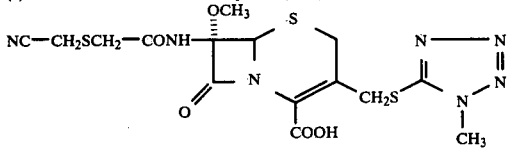

(2) All the amino acids were the L-isomers.
(3) In Comparative Example Compound (VIII) was employed in the absorption test.

EXAMPLE 35

7-[1-(1H)-tetrazolylacetamido]-3-[2-(5-methyl-1,3,4-thiazolyl)-thiomethyl]-3-cephem-4-carboxylic acid L-leucyl-L-lysyloxymethyl ester hydrochloric acid salt having the following formula was prepared in accordance with the following method.

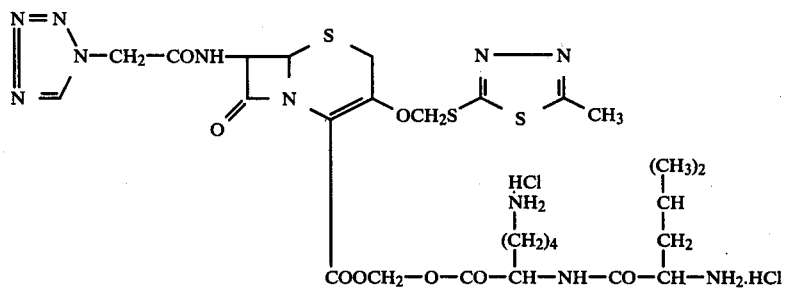

In 30 ml of N,N-dimethylformamide were dissolved 2.0 g of α-tert-butyloxycarbonyl-L-leucyl-ε-tert-butyloxycarbonyl-L-lysine and 0.45 g of triethylamine. To the solution was added 0.77 g of chloroiodomethane and the mixture was stirred at 20° C. for 25 hours. Most N,N-dimethylformamide was removed under reduced pressure, and to the residue thus obtained was added 50 ml of a mixed liquid consisting of ethyl acetate and water in a volume ratio of 1:1. After thoroughly shaking the mixed solution, the ethyl acetate layer was washed with a 5% aqueous sodium hydrogencarbonate solution and dried with anhydrous magnesium sulfate. Then, the ethyl acetate was removed under reduced pressure and the residue thus obtained was subjected to silica gel chromatography to separate 2.0 g of (α-tert-butyloxycarbonyl-L-leucyl-ε-tert-butyloxycarbonyl-L-lysyl)-chloromethyl ester.

To 40 ml of an acetone solution containing 2.0 g of (α-tert-butyloxycarbonyl-L-leucyl-ε-tert-butyloxycarbonyl-L-lisyl)chloromethyl ester was added 1.2 g of sodium iodide, and the reaction was carried out with stirring in a nitrogen gas atmosphere for 17 hours to separate sodium chloride. The sodium chloride was removed by filtration and the filtrate was concentrated under reduced pressure. The residue thus obtained was dissolved in ether and insolubles were removed by filtration. After removing the ether from the filtrate, the filtrate was dissolved in 20 ml of N,N-dimethylformamide. The solution was added to 40 ml of a N,N-dimethylformamide solution containing 2.5 g of sodium 7-[1-(1H)-tetrazolylacetoamido]-3-[2-(5-methyl-1,3,4-thiazolyl)thiomethyl]-3-cephem-carboxylate and the reaction was carried out at 20° C. for 6 hours. After completion of the reaction, part of N,N-dimethylformamide was removed and to the reaction mixture were added 100 ml of water and ethyl acetate as the extraction liquid. The ethyl acetate layer was washed with a 1N aqueous hydrochloric acid solution, a 10% aqueous sodium hydrogencarbonate solution and a saturated sodium chloride solution, and dried with anhydrous magnesium sulfate. Then, the ethyl acetate was removed from the layer to give solid residue.

The residue thus obtained was added to 30 ml of trifluoroacetic acid and the reaction was carried out at 0° C. with stirring 20 minutes. After completion of the reaction, excess trifluoroacetic acid was removed under reduced pressure. The residue thus obtained was dissolved in ethyl acetate and the solution was washed twice with an aqueous sodium hydrogencarbonate solution and then twice with a saturated sodium chloride solution. The ethyl acetate layer was dried with anhydrous magnesium sulfate and added with ester saturated with anhydrous hydrogen chloride. The solvents were removed under reduced pressure to give 1.6 g of a compound.

The compound thus obtained was identified as 7-[1-(1H)-tetrazolylacetoamido]-3-[2-(5-methyl-1,3,4-thiazolyl)thiomethyl]-3-cephem-4-carboxylic acid L-leucyl-L-lysyloxymethyl ester hydrochloric acid salt by the following NMR spectrum of the compound.

NMR spectrum (in DMSO substituted by heavy hydrogen):

| | | |
|---|---|---|
| 0.81 ppm | CH$_3$\\CH—/CH$_3$ | doublet |
| 1.42 ppm | CH$_3$\\CH—CH$_2$—/CH$_3$ | multiplet |
| 2.68 ppm | —CH$_2$S-(N=N/S)-CH$_3$ | singlet |
| 1.77 ppm | \\CH—(CH$_2$)$_3$—CH$_2$NH$_2$/ | multiplet |
| 3.62 ppm | —N-(S/COOH)-H,H | multiplet |
| 4.41 ppm | —CH$_2$S-(N=N/S)-CH$_3$ | multiplet |
| 5.06 ppm | 6-H | doublet |
| 5.36 ppm | N=N\\N—CH$_2$—/N= | singlet |
| 5.65 ppm | 7-H | multiplet |

9.22 ppm — N=N, N—, N=, H — singlet 9.50 ppm — —CONH— (β-lactam structure) — doublet The absorption test results of 7-[1-(1H)-tetrazolylacetoamido]-3-[2-(5-methyl-1,3,4-thiazolyl)thiomethyl]-3-cephem-4-carboxylic acid L-leucyl-L-lysyloxymethyl ester hydrochloric acid salt are shown in Table 9.

EXAMPLES 36-38

The same procedures are described in Example 35 were repeated except that other oligopeptides were employed instead of the α-tert-butyloxycarbonyl-L-leucyl-ε-tert-butyloxycarbonyl-L-lysine. As a result, the cephalosporin derivatives having the oligopeptides as set forth in Table 9 were obtained. The absorption test results of the compounds thus obtained are shown in Table 9.

TABLE 9

| Example No. | Oligopeptide | | | Blood Concentration of Compound (IX) (μg/ml) | | | |
|---|---|---|---|---|---|---|---|
| | X | Amino Acid Unit Containing $R_1$ | Amino Acid Unit Containing $R_2$ | n | 0.5 hr | 1 hr | 2 hrs. | 4 hrs. |
| 35 | H | Leu | Lys | 1 | 5.64 | 3.84 | 1.87 | 0.74 |
| 36 | H | Leu | Phe | 1 | 5.34 | 4.74 | 3.94 | 2.41 |
| 37 | H | α-AAA | Phe | 1 | 1.53 | 1.00 | 0.41 | 0.23 |
| 38 | H | PheGly(D) | Phe | 1 | 1.49 | 0.89 | 0.32 | 0.18 |
| Comparative | | (None) | | | 1.12 | 0.63 | 0.23 | 0.11 |

Note:
(1) The chemical formula of Compound (IX) is as follows:

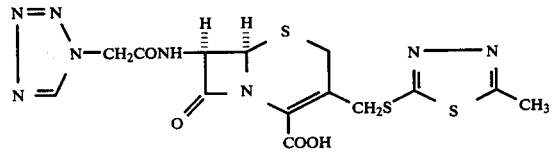

(2) (D) shows the D-isomer of the amino acid. Amino acids without the indication show the L-isomers.
(3) In Comparative Example Compound (IX) was employed in the absorption test.

What is claimed is:

1. An antibacterial composition having enhanced intestinal absorption comprising a pharmacologically effective amount of an antibacterially active 7-aminocephalosporanic acid derivative having bonded thereto, at any side chain at the 3-, 4-, or 7-position, a group having the general formula (I)

wherein
X is a hydrogen atom, $C_{1-15}$ alkyl group, $R_3CO$ group wherein $R_3$ is a hydrogen atom or a straight or branched chain $C_{1-15}$ alkyl group or a protective group easily removable by acid hydrolysis, hydrogenolysis or enzyme existing in a living body;
$R_1$ and $R_2$ each independently is a side chain of an amino acid constituting the group having the general formula (I) wherein the amino acid having $R_1$ or $R_2$ as the side chain is alanine, isoleucine, leucine, methionine, valine, phenylalanine, tyrosine, phenylglycine, tryptophan, lysine, ornithine, histidine, arginine, serine, threonine, glutamic acid, aspartic acid, cysteine, α-aminoadipic acid, proline, α-amino-n-butyric or glycine; and n is an integer of 1 to 3 and a pharmaceutically acceptable carrier.

2. The antibacterial composition of claim 1, wherein X is a hydrogen atom or a formyl group.

3. The antibacterial composition of claim 1, wherein the amino acid constituting the group having the general formula (I) is a L-amino acid.

4. The antibacterial composition of claim 1, wherein n is one.

5. The antibacterial composition of claim 1, wherein the 7-aminocephalosporanic acid derivative is represented by the general formula (II):

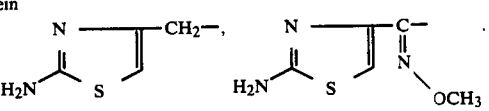

wherein
$R_4$ is

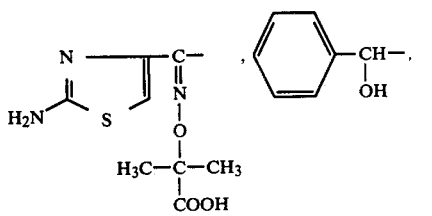

-continued

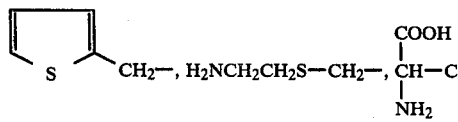

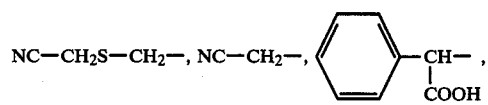

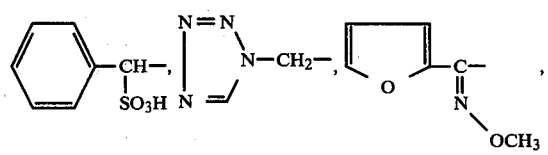

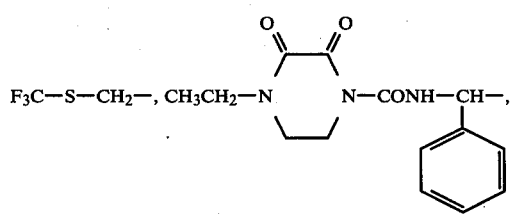

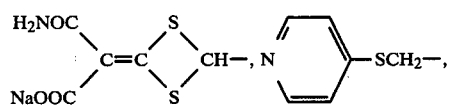

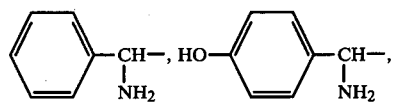

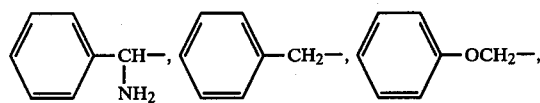

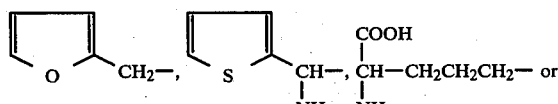

$R_5$ is a hydrogen atom or a methoxy group;
$R_6$ is —$CH_3$, —Cl, —$OCH_3$, —H, $CH_2OCOCH_3$,

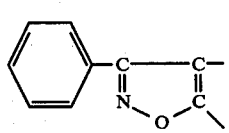

or —$CH_2SHet$. wherein Het. is a 5- to 6-membered heterocyclic ring containing therein 1 to 4 nitrogen, oxygen or sulfur atoms; and $R_7$ is a hydrogen atom, an alkali metal, an alkaline earth metal, an organic amino group or a protective group for the carboxyl group.

6. A method for modifying a cephalosporin derivative to improve the intestinal absorption of said cephalosporin derivative comprising bonding a group having the general formula (I):

$$X{\mathrel{+}}NH-\overset{R_1}{CH}-CO{\mathrel{\overline{)_n}}}NH-\overset{R_2}{CH}-CO- \qquad (I)$$

wherein

X is a hydrogen atom, $C_{1-15}$ alkyl grup, $R_3CO$-group wherein $R_3$ is a hydrogen atom or a straight or branched chain $C_{1-15}$ alkyl group or a protective group easily removable by acid hydrolysis, hydrogenolysis or enzyme existing in a living body;

$R_1$ and $R_2$ each independently is a side chain of an amino acid constituting the group having the general formula (I), wherein the amino acid having $R_1$ or $R_2$ as the side chain is alanine, isoleucine, leucine, methionine, valine, phenylalanine tyrosine, phenylglycine, tryptophan, lysine, ornithine, histidine, arginine, serine, threonine, glutamic acid, aspartic acid, cysteine, α-aminoadipic acid, proline, α-amino-n-butyric acid or glycine; and n is an integer of 1 to 3, to any side chain at the 3-, 4- or 7-position of a 7-aminocephalosporanic acid derivative having antibacterial activity.

7. The method of claim 1, wherein X is a hydrogen atom or a formyl group.

8. The method of claim 1, wherein the amino acid constituting the group having the general formula (I) is a L-amino acid.

9. The method of claim 1, wherein n is one.

10. The method of claim 1, wherein the 7-aminocephalosporanic acid derivative is represented by the general formula (II):

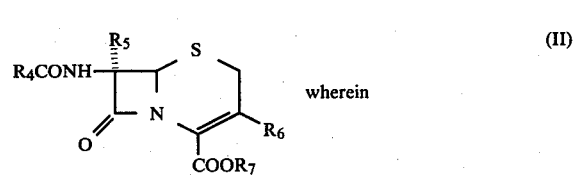

wherein $R_4$ is

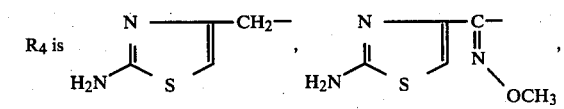

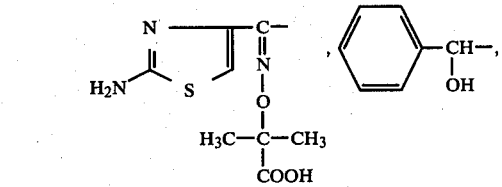

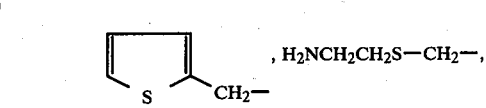

COOH
|
CH—$CH_2S$—$CH_2$—, NC—$CH_2S$—$CH_2$—, NC—$CH_2$—,
|
$NH_2$

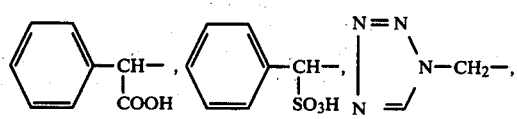
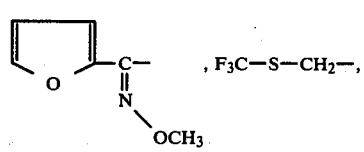
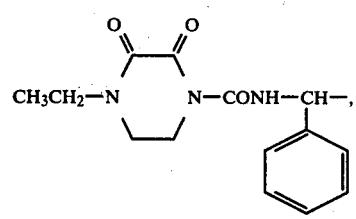
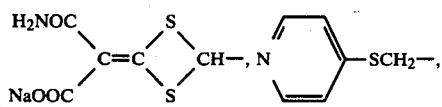
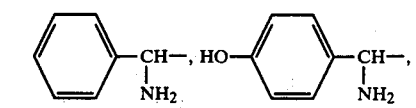
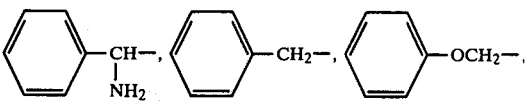
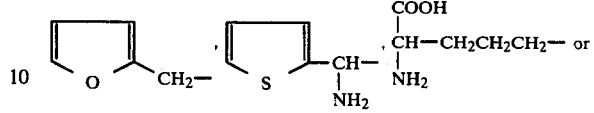
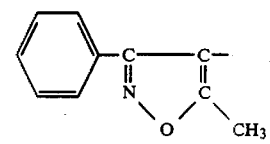
$R_5$ is a hydrogen atom or a methoxy group;
$R_6$ is —$CH_3$, —Cl, —$OCH_3$, —H, —$CH_2OCOCH_3$,
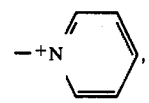
—$CH_2OCONH_2$ or —$CH_2SHet$. wherein Het. is a 5- to 6-membered heterocyclic ring containing therein 1 to 4 nitrogen, oxygen or sulfur atoms; and
$R_7$ is a hydrogen atom, an alkali metal, an alkaline earth metal, an organic amino group or a protective group for the carboxyl group.
* * * * *